United States Patent
Ito et al.

(10) Patent No.: US 10,570,351 B2
(45) Date of Patent: Feb. 25, 2020

(54) HYGIENE FRAGRANCE COMPOSITIONS

(71) Applicant: TAKASAGO INTERNATIONAL CORPORATION, Tokyo (JP)

(72) Inventors: Hiroki Ito, Singapore (SG); Miyuki Takayanagi, Kanagawa (JP); Kaori Takahashi, Kanagawa (JP); Kanetoshi Ito, Kanagawa (JP); Jeffrey Schmoyer, Hillsdale, NJ (US); Jonathan Warr, Paris (FR)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 8 days.

(21) Appl. No.: 15/745,346

(22) PCT Filed: Jul. 20, 2016

(86) PCT No.: PCT/US2016/043214
§ 371 (c)(1),
(2) Date: Jan. 16, 2018

(87) PCT Pub. No.: WO2017/015408
PCT Pub. Date: Jan. 26, 2017

(65) Prior Publication Data
US 2019/0093045 A1 Mar. 28, 2019

Related U.S. Application Data

(60) Provisional application No. 62/194,790, filed on Jul. 20, 2015.

(51) Int. Cl.
| | | |
|---|---|---|
| *A61K 8/00* | (2006.01) | |
| *A61K 8/18* | (2006.01) | |
| *C11B 9/00* | (2006.01) | |
| *A61L 2/16* | (2006.01) | |
| *A61L 9/013* | (2006.01) | |
| *A61L 9/14* | (2006.01) | |
| *C11D 3/50* | (2006.01) | |

(52) U.S. Cl.
CPC .............. *C11B 9/0034* (2013.01); *A61L 2/16* (2013.01); *A61L 9/013* (2013.01); *A61L 9/14* (2013.01); *C11B 9/00* (2013.01); *C11B 9/0011* (2013.01); *C11B 9/0015* (2013.01); *C11D 3/50* (2013.01)

(58) Field of Classification Search
CPC ... C11B 9/0034; C11B 9/0011; C11B 9/0015; C11B 9/00; C11B 9/013; A61L 9/14; A61L 9/013; A61L 2/16; C11D 3/50
USPC ......................................................... 512/2, 1
See application file for complete search history.

(56) References Cited

U.S. PATENT DOCUMENTS

| | | | |
|---|---|---|---|
| 2004/0037792 A1* | 2/2004 | Hiramoto ................ | A23G 3/36 424/65 |
| 2007/0042934 A1* | 2/2007 | Fadel ...................... | A61K 8/18 512/1 |

FOREIGN PATENT DOCUMENTS

EP 2 014 273 A1 1/2009

OTHER PUBLICATIONS

International Search Report and Written Opinion dated Sep. 30, 2016 in International Application No. PCT/US2016/043214, 13 pages.
International Preliminary Report on Patentability dated Jan. 23, 2018 in International Application No. PCT/US2016/043214, 8 pages.
Kerr et al., "Odors and the Perception of Hygiene," Perceptual and Motor Skills, 100:135-141 (2005).
Knoeferle et al., "That Sounds Sweet: Using Cross-Modal Correspondences to Communicate Gustatory Attributes," Psychology and Marketing, vol. 32(1): 107-120, Jan. 2015.
Strugnell et al., "Consumer Perceptions and opinions of fragrances in household products," Nutrition & Food Science, [Online] 99(4) (1999) Retrieved from the Internet: URL:http://www.emeraldinsight.com/doi/full/10.1108/nfs.1999.01799daf.002> (Accessed on May 4, 2018).

* cited by examiner

*Primary Examiner* — Jessica Whiteley
(74) *Attorney, Agent, or Firm* — Baker Botts L.L.P.

(57) ABSTRACT

Fragrance accords are provided herein that can provide a consumer with a perception of hygiene. The fragrance accords can include one or more of a citrus compound, floral compound, herbal/aromatic compound, and sulfur containing compound. The accords are suitable for incorporation into a fragrance composition and/or a consumer product to enhance the perception of hygiene. Methods of stimulating the perception of hygiene with the fragrance accords are also provided.

19 Claims, 30 Drawing Sheets

HYGIENE FRAGRANCE COMPOSITIONS

CROSS-REFERENCE TO RELATED APPLICATIONS

This application is a U.S. National Stage Patent Application under 35 U.S.C. § 371 of International Application No. PCT/US2016/043214, filed on Jul. 20, 2016, which claims priority to U.S. Provisional Application No. 62/194,790, filed Jul. 20, 2015, the contents of each of which are incorporated by reference herein in their entirety.

FIELD

The present disclosure relates to specific fragrance compositions comprising one or more accords, which elicit a consumer's perception of hygiene. The compositions are incorporated into consumer products to stimulate a consumer's perception of hygiene and/or hygienic conditions.

BACKGROUND

Fragrances can be incorporated into consumer products to both provide fragrance to the objects being treated, as well as provide fragrance to the consumer during use or application. For example, a cleaning wipe containing a fragrance compound may both deposit fragrance on the surface being cleaned and also release fragrance, which is inhaled by the user during the act of cleaning the surface.

It is known that a fragrance can trigger a specific perception in the consumer regarding the quality and effectiveness of the consumer product. Research has shown that consumer perception of the efficacy of cleaning products can be modified by inclusion of a pleasant scent. For consumer products such as cleaners, deodorizers, soaps, sanitizers, and air fresheners, it is desirable that the fragrance provides the user with perceptions not only of cleaning efficacy, but of asepsis, hygiene, or the absence of undesirable biological microorganisms. However, the ingredients which are known to drive hygienic perception are quite specific, and often perceived as harsh, and limit the ability to create diverse complex and pleasant scents. Examples include lemon oil, cloves, *eucalyptus*, and chlorine bleach, most of which actually have some inherent antiseptic properties. Therefore, there remains a need to identify fragrances and accords that actually stimulate a consumer's perception of hygiene while also remaining sufficiently complex, pleasant and not overtly indicative of a particular antiseptic ingredient, so as to not limit the ability to create products that offer a diverse array of pleasant scents. The present disclosure addresses this need in further detail below.

SUMMARY OF THE INVENTION

The present disclosure relates to fragrance compositions comprising one or more accords that elicit a consumer's perception of hygiene. In certain embodiments the fragrance compositions are incorporated into consumer products to stimulate or elicit a consumer's perception of hygiene at the location where the consumer product is used.

In certain embodiments, the present disclosure provides a fragrance accord comprising one or more compounds selected from the group consisting of a citrus compound, an herbal/aromatic compound, a fruity compound, a sulfur containing compound, and combinations thereof.

For example, a citrus compound can be present in an amount of greater than 30% by weight. Alternatively or additionally, an herbal/aromatic compound can be present in an amount of less than 50% by weight. Alternatively or additionally, a fruity compound can be present in an amount of less than 5% by weight.

Where both a citrus compound and an herbal/aromatic compound are present, the ratio between the citrus compound and the herbal/aromatic compound can be from about 7:1 to about 0.65:1. An accord can comprise both a citrus compound and sulfur compound. Alternatively or additionally, an accord can comprise both a fruity compound and a sulfur containing compound.

In certain embodiments, the compound is a sulfur containing compound selected from the group consisting of limonene thiol, thiogeraniol, RINGONOL®, oxane, p-menthene-8-thiol, and combinations thereof. The fragrance accord can further include at least one additional sulfur containing compound selected from the group consisting of 4-methylthio-4-methyl-2-pentanone, 3 mercapto-hexanol, methoxymethylbutanethiol, dibutyl sulfide, dimethyl sufide, thiocineol, 2-isopropyl-4-methylthiazole, and combinations thereof.

The present disclosure further provides fragrance compositions comprising at least one fragrance accord as disclosed herein. In certain embodiments, the fragrance accord can be present in an amount of from about 0.001% to about 100% by weight of the fragrance composition. In particular embodiments, the fragrance accord can be present in an amount of from about 20% to about 25% by weight of the fragrance composition. The fragrance composition can include one or more sulfur containing compounds in an amount from about 0.005% to about 0.1% by weight of the fragrance composition. For example, the one or more sulfur containing compounds can be at least one of limonene thiol in an amount from about 0.000005% to about 0.00025% by weight of the fragrance composition, thiogeraniol in an amount from about 0.00002% to about 0.001% by weight of the fragrance composition, RINGONOL® in an amount from about 0.0005% to about 0.025% by weight of the fragrance composition, oxane in an amount from about 0.001% to about 0.05% by weight of the fragrance composition, and p-menthene-8-thiol in an amount from about 0.0005% to about 0.025% by weight of the fragrance composition.

In certain embodiments, a fragrance accord and/or a fragrance composition can be incorporated into a consumer product base or consumer product.

The present disclosure further provides methods of stimulating a perception of hygiene in a consumer. In certain embodiments, a method of stimulating a perception of hygiene in a consumer can include administering a fragrance accord and/or a fragrance composition in an amount effective to stimulate the perception of hygiene.

The present disclosure further provides methods of making a consumer product capable of stimulating a perception of hygiene in a consumer. A method of making a consumer product capable of stimulating a perception of hygiene in a consumer can include providing at least one consumer product base and combining the consumer product base with a fragrance accord and/or a fragrance composition.

BRIEF DESCRIPTION OF THE DRAWINGS

FIG. 7A shows the scoring for perceived hygienic attribute. FIG. 7B shows the scoring for the perceived clean attribute. FIG. 7C shows the scoring for the perceived proud attribute.

FIG. 8A show perceived hygiene scores. FIG. 8B shows perceived cleanliness scores. FIG. 8C shows perceived proud scores.

FIG. 8D shows direct odor assessment of hedonicity scores. FIG. 8E shows direct odor assessment of hygiene scores. FIG. 8F shows direct odor assessment of intensity scores.

FIG. 9A show perceived germ removal scores. FIG. 9B shows perceived germ kill scores. FIG. 9C shows perceived cleanliness scores.

FIG. 9D shows direct odorant assessment of hedonicity scores. FIG. 9E shows direct odorant assessment of cleanliness scores. FIG. 9F shows direct odorant assessment of intensity scores.

DETAILED DESCRIPTION

Figure 1:
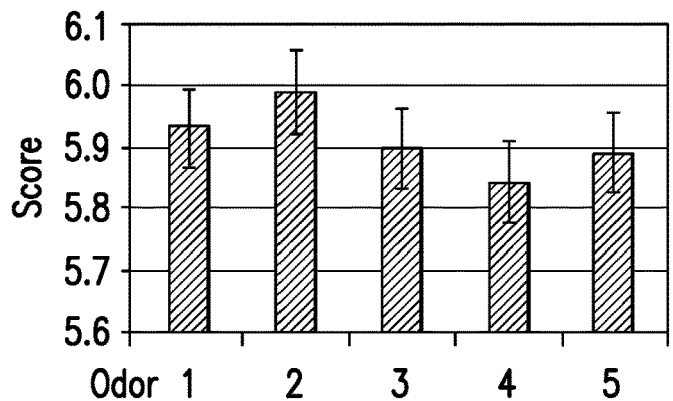
FIG. 1 depicts the average attribute score for perceived germ removal as perceived based on kitchen images in the presence of the different odors of Example 4.

As discussed above, there is a need in the art to identify accords that can be used in fragrance compositions and in consumer products to stimulate a consumer's perception of hygiene. The presently disclosed subject matter addresses this need through a fragrance composition comprising at least one fragrance accord. Specifically, the presently disclosed subject matter provides a means of eliciting in consumers, both consciously and subconsciously, a strongly felt hygiene perception via set of unique fragrance formulation parameters, which in turn also affords a wide range of pleasant and complex fragrance experiences not directly linked to any particular historic antiseptic ingredient.

1. Definitions

The terms used in this specification generally have their ordinary meanings in the art, within the context of this disclosure and in the specific context where each term is used. Certain terms are discussed below, or elsewhere in the specification, to provide additional guidance to the practitioner in describing the compositions and methods of the disclosure and how to make and use them.

As used herein, the use of the word "a" or "an" when used in conjunction with the term "comprising" in the claims and/or the specification may mean "one," but it is also consistent with the meaning of "one or more," "at least one," and "one or more than one." Still further, the terms "having," "including," "containing" and "comprising" are interchangeable and one of skill in the art is cognizant that these terms are open ended terms.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As used herein, the term "fragrance" is taken to mean a material, e.g., a fragrance composition that may contain an accord. It is also understood that a "fragrance" can be a mixture of individual materials, such as, for example, multiple accords or a fully formulated fragrance.

As used herein, the term "accord" or "fragrance accord" refers to a formulation that contains one or more different compounds that creates a specific smell, odor or scent, and that causes a specific perception, feeling and/or physiological effect when used in proper effective amounts as necessary.

As used herein, the term "hygiene" refers to a consumer's perception of hygienic conditions. Hygiene perception can be defined as a more deeply felt sense of asepsis or the absence of germs and/or other pathogens on a consumer targeted cleaning site as demonstrated by consumer testing. For example, a consumer may identify attributes such as a product leaving surfaces free of bacteria or microbes, antiseptic conditions, germ removal or germ kill with a perception of hygiene. A consumer would perceive hygiene as more robust than a clean perception.

As used herein, the term "clean" refers to a consumer's perception of clean conditions. For example, a consumer may identify attributes such as freshness, removal of tough food, grease, dirt and/or grime, or clear and/or shining surfaces with a perception of clean.

As used herein, the term "proud" or "pride" refers to a consumer's perception of being proud or having pride. For example, a consumer may feel a deeper sense of pride to invite friends and/or family into their home.

As used herein, the term "hedonicity" refers to a consumer's overall opinion of an odor, for example, whether a consumer finds an odor to be pleasant or generally likeable.

The terms used herein to describe a consumer's perception, although expressed in the English language, can correspond to words in a foreign language, e.g., Japanese, and incorporate any additional meaning, implication, connotation, and/or nuance from that language. For example, "clean" as used herein can correspond to the Japanese word "seiketsu." "Germ removal" as used herein can correspond to the Japanese word "jokin." "Germ kill" as used herein can correspond to the Japanese word "sakkin."

As used herein, the term "subject" refers to a human or a non-human subject. A "consumer" refers to a human subject. Non-limiting examples of non-human subjects include non-human primates, dogs, cats, mice, rats, guinea pigs, rabbits, pigs, fowl, horses, cows, goats, sheep, cetaceans, etc.

As used herein, the term "consumer product base" means a composition for use as a consumer product to fulfill the specific purpose of the consumer product, such as cleaning, softening, caring or the like.

As used herein, the term "enantiomers" refers to a pair of stereoisomers that are non-superimposable mirror images of each other. A 1:1 mixture of a pair of enantiomers is a "racemic" mixture. The term is used to designate a racemic mixture where appropriate.

As used herein, the term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro or levorotatory) which they rotate plane polarized light at the wavelength of the sodium D line. The compounds of the presently disclosed subject matter contain one or more asymmetric centers and may thus give rise to enantiomers, diastereomers, and other stereoisomeric forms that may be defined, in terms of absolute stereochemistry, as (R)- or (S)-. The presently disclosed subject matter is meant to include all such possible isomers, including racemic mixtures, optically pure forms and intermediate mixtures. Optically active (R)- and (S)- isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "isomers" refers to different compounds that have the same molecular formula but differ in arrangement and configuration of the atoms. Also as used herein, the term "stereoisomer" refers to any of the various stereo isomeric configurations which may exist for a given compound of the presently disclosed subject matter and includes geometric isomers. It is understood that a substituent may be attached at a chiral center of a carbon atom. Therefore, the presently disclosed subject matter includes enantiomers, diastereomers or racemates of the compound. Also as used herein, the terms "constitutional isomers" refers to different compounds which have the same numbers of, and types of, atoms but the atoms are connected differently.

2. Accords and Compositions

An accord includes, but is not limited to, two or more compounds. In a non-limiting example, an accord and/or fragrance composition includes, but is not limited to, one or more compounds in combination selected from one or more groups of fragrance compounds characterized by their respective odor properties, e.g., one or more citrus compound(s), and/or one or more herbal/aromatic compound(s), and/or one or more fruity compound(s), and/or one or more green compounds(s), and/or one or more floral compound(s), and/or combinations thereof. The accords and/or fragrance compositions of the presently disclosed subject matter can be further characterized by one or more methods described herein to ascertain measurements of perception of hygiene.

In certain embodiments, the one or more citrus compounds include, but are not limited to, citrus oils or extracts such as orange, lime, grapefruit, *litsea cubeba* essential oils, concentrated citrus oils (folded oils), citronellol (3,7-dimethyloct-6-en-1-ol) [CAS No. 106-22-9], cymene, para (1-methyl-4-propan-2-ylbenzene) (or 1-methyl-4-(1-methylethyl)benzene) [CAS No. 99-87-6]. dodecane nitrile [CAS No. 2437-25-4], citronellyl nitrile (3,7-Dimethyl-6-octenenitrile) [CAS No. 51566-62-2], clonal, limonene (1-methyl-4-(1-methylethenyl)-cyclohexene) [CAS No. 138-86-3], citral ((2E)-3,7-dimethylocta-2,6-dienal) [CAS Nos. 141-27-5, 5392-40-5], iso-cyclo citral (2,4,6-trimethyl-cyclohex-3-ene-1-carbaldehyde) [CAS No. 1335-66-6], nerol ((2Z)-3,7-dimethylocta-2,6-dien-1-ol) [CAS No. 106-25-2], citronellal (3,7-dimethyloct-6-enal) [CAS No. 106-23-0], Dihydromyrcenol [CAS No. 18479-58-8], farnesene, nopol (2-(6,6-dimethyl-4-bicyclo[3.1.1]hept-3-enyl)ethanol) [CAS No. 128-50-7], mandarin aldehyde (trans-2-Dodecenal) [CAS No. 20407-84-5], nopyl acetate (2-(6,6-Dimethyl-bicyclo[3.1.1]hept-2-ene-2-yl) ethyl acetate) [CAS No. 128-51-8], oxane (e.g., 1,3-Oxathiane, 2-methyl-4-propyl-, cis-, [CAS No. 0059323-76-1]), limonene thiol, grapefruit mercaptan, citrathal, lime oxide, elemi oil, and other essential oils, extract fractions or isolates containing >50% limonene, or >50% citral, or >50% citronellal compounds by weight, and combinations thereof. The compounds here include constitutional isomers, enantiomers, stereoisomers and racemic mixtures of said compounds listed herein.

In certain embodiments, the one or more herbal/aromatic compounds include, but are not limited to, bornyl acetate ((4,7,7-trimethyl-3-bicyclo[2.2.1]heptanyl) acetate) [CAS No. 125-12-2], iso-bornyl acetate ([(1R,3S,4S)-4,7,7-trimethyl-3-bicyclo[2.2.1]heptanyl] acetate) [CAS No. 125-12-2], pinene alpha (6,6-trimethylbicyclo[3.1.1]hept-3-ene) [CAS No. 80-56-8], pinene beta (6,6-dimethyl-4-methylidenebicyclo[3.1.1]heptane) [127-91-3], pine oils, terpinolene 20 (1-methyl-4-propan-2-ylidenecyclohexene) [CAS Number: 586-62-9], terpinolene 90 (1-methyl-4-propan-2-ylidenecyclohexene) [CAS Number: 586-62-9], terpinene alpha (1-Isopropyl-4-methyl-1,3-cyclohexadiene) [CAS No. 99-86-5], alpha-terpineol (2-(4-methylcyclohex-3-en-1-yl) propan-2-ol) [CAS No. 98-55-5], terpine gama (1-methyl-4-propan-2-ylcyclohexa-1,4-diene) [CAS No. 99-85-4], DH terpineol (2-(4-methylcyclohexyl)propan-2-ol) [CAS No. 58985-02-7], terpinol, terpinyl acetate ((±)-2-(4-Methyl-3-cyclohexenyl)isopropyl acetate) [CAS No. 80-26-2], terpineol (2-(4-methylcyclohex-3-en-1-yl)propan-2-ol) [CAS No. 98-55-5], Linalool (3,7-Dimethyl-1,6-octadiene-3-ol) [CAS No. 78-70-6 11024-20-7], linalyl esters such as linalyl acetate (3,7-dimethylocta-1,6-dien-3-yl acetate) [CAS No. 115-95-7], and essential oils or extracts containing >50% linalool and linalyl acetate combined (i.e., lavender oils) by weight, thymol (5-methyl-2-propan-2-ylphenol) [CAS No. 89-83-8] (e.g., thymol crystals), essential oils or extracts containing >50% thymol by weight, essential oils containing a combination of >50% of pinene alpha and pinene beta combined by weight, and combinations thereof. The compounds here include constitutional isomers, enantiomers, stereoisomers and racemic mixtures of said compounds listed herein.

In certain embodiments, the one or more fruity compounds include, but are not limited to, cassis, raspberry ketone (4-(4-Hydroxyphenyl)-2-butanone) [CAS No. 5471-51-2], esters of aliphatic saturated linear or branched fatty acids with a number of carbon atoms from $C_2$-$C_7$, reacted with aliphatic saturated or unsaturated linear or branched alcohols with a number of carbon atoms from $C_1$-$C_7$, and combinations thereof. In certain embodiments, the total number of carbon atoms is less than 12. In certain embodiments, the total number of carbon atoms is less than 10. Additional non-limiting examples of fruity compounds include, but is not limited to $C_1$-$C_6$ linear or branched alkyl acetates, propionates, butyrates, iso-butyrayes, pentanoates (valerate), iso-valerates, glycolates, hexanoates, heptanoates, crotonates and tiglates. The compounds here include constitutional isomers, enantiomers, stereoisomers and racemic mixtures of said compounds listed herein.

In certain embodiments, the one or more floral compounds include, but are not limited to, Citronellyl Acetate (3,7-dimethyloct-6-enyl acetate) [CAS Number: 150-84-5]; Dimethyl Anthranilate (methyl 2-methylaminobenzoate) [CAS Number: 85-91-6]; Eugenol (2-Methoxy-4-(2-propen-1-yl)-phenol) [CAS Number: 97-53-0]; Indole Crystals (1H-indole) [CAS Number; 120-72-9]; Methyl Anthranilate (Benzoic acid, 2-amino-, methyl ester) [CAS Number: 134-20-3], Methyl Jasmonate (methyl 2-(3-oxo-2-pent-2-enylcyclopentyl)acetate) [CAS Number: 39924-52-2]; and combinations thereof. The compounds here include constitutional isomers, enantiomers, stereoisomers and racemic mixtures of said compounds listed herein. In certain embodiments, the one or more green compounds include, but are not limited to, Dynascone Neat 939.745 (1-(2,6,6-Trimethyl-1,3-cyclohexadien-1-yl)-2-butene-1-one) [CAS Number: 23696-85-7]; *Galbanum* Oil A Nat (ferula galbaniflua resin oil) [CAS Number: 8023-91-4]; Hexen-1-ol, Cis-3 ((Z)-hex-3-en-1-ol) [CAS Number: 928-96-1 95123-47-0]; Hexenal, Trans-2 ((E)-hex-2-enal) [CAS Number: 6728-26-3]; and combinations thereof. The compounds here include constitutional isomers, enantiomers, stereoisomers and racemic mixtures of said compounds listed herein.

In certain embodiments, the one or more citrus, herbal/aromatic, fruity, floral, and/or green compounds are formulated in an accord in amounts from about 0.001% to about 99% by weight, or from about 0.01% to about 90% by weight, or from about 0.1% to about 80% by weight, or from about 1% to about 70% by weight, or from about 2% to about 60% by weight, or from about 5% to about 50% by weight, or from about 10% to about 40% by weight, or from about 15% to about 30% by weight, or from about 20% to about 25% by weight.

In certain embodiments, the one or more citrus compounds are present in an accord at an amount from about 0.1% to about 80% by weight, or from about 0.2% to about 50% or from about 0.2% to about 60% by weight. In alternate embodiments, the one or more citrus compounds are formulated in an accord in amounts of more than about 30%, more than about 40%, or more than about 50% by weight.

In certain embodiments, the one or more herbal/aromatic compounds are formulated in an accord in amounts of from about 0.1% to about 80%, or from about 0.1% to about 50%, or from about 0.2% to about 37% or from about 0.5% to about 35% by weight. In alternate embodiments, the one or more herbal/aromatic compounds are present in an accord in amounts of less than about 50%, or less than about 30% by weight.

In certain embodiments, the one or more fruity compounds are formulated in an accord in amounts of from about 0.1% to about 10%, or from about 0.1% to about 5% by weight. In alternative embodiments, the one or more fruity compounds are present in an accord in amounts of less than or equal to about 5% by weight.

In certain embodiments, the remainder of the compounds in the accord should constitute less than about 50%, or less than about 25%, by weight.

In certain embodiments, one or more citrus, herbal/aromatic, and fruity compounds are formulated in an accord. In certain embodiments, the one or more citrus compounds are formulated in an accord in amounts of more than about 30%, more than about 40%, or more than about 50% by weight. In certain embodiments, the one or more herbal/aromatic compounds are formulated in an accord in amounts of less than about 50%, or less than about 30% by weight. In certain embodiments, the one or more fruity compounds are formulated in an accord in amounts of less than or equal to about 5% by weight.

In certain embodiments, the ratio of citrus to herbal/aromatic compounds is from about 10:1 to about 0.1:1, or from about 7:1 to about 0.65:1. In certain embodiments, the ratio of citrus to herbal/aromatic compounds is from about 5:1 to about 1:1.

In certain embodiments, a fragrance composition can comprise one or more accords, and/or one or more compounds of the presently disclosed subject matter. In certain embodiments, the fragrance compositions can comprise two or more accords, and/or two or more compounds. In certain embodiments, the fragrance compositions of the present disclosure comprise or three or more accords, or four fragrance accords. Likewise, in certain embodiments, the fragrance compositions of the present disclosure comprise three or more compounds, or four fragrance compounds. In specific embodiments, the fragrance compositions of the presently disclosed subject matter comprise at least one citrus compound, and at least one or more of an herbal/aromatic compound, fruity compound, green compound, and/or floral compound, and combinations thereof.

In certain embodiments, the one or more compounds are formulated in a fragrance composition in amounts from about 0.0001% to about 100% by weight, or from about 0.0001% to about 80%, or from about 0.0001% to about 25%, or from about 0.01% to about 90% by weight, or from about 0.1% to about 80% by weight, or from about 0.01% to about 50%, or from about 1% to about 70% by weight, or from about 2% to about 60% by weight, or from about 5% to about 50% by weight, or from about 10% to about 40% by weight, or from about 15% to about 30% by weight, or from about 20% to about 25% by weight. In alternate embodiments, the one or more compounds are formulated in a composition in amounts from about 1.0% to about 100% by weight, or from about 10% to about 100% by weight, or from about 20% to about 100% by weight, or from about 30% to about 100% by weight, or from about 40% to about 100% by weight, or from about 50% to about 100% by weight, or from about 60% to about 100% by weight, or from about 70% to about 100% by weight, or from about 80% to about 100% by weight, or from about 85% to about 100% by weight, or from about 90% to about 100% by weight.

In certain embodiments, the accords are formulated in a fragrance composition at an amount from about 0.001% to about 100% by weight, or from about 0.001% to about 99% by weight, or from about 0.01% to about 90% by weight, or from about 0.1% to about 80% by weight, or from about 1% to about 70% by weight, or from about 2% to about 60% by weight, or from about 5% to about 50% by weight, or from about 10% to about 40% by weight, or from about 15% to about 30% by weight, or from about 20% to about 25% by weight. In alternate embodiments, the accords are formulated in a composition at an amount from about 1.0% to about 99% by weight, or from about 10% to about 99% by weight, or from about 20% to about 99% by weight, or from about 30% to about 99% by weight, or from about 40% to about 99% by weight, or from about 50% to about 99% by weight, or from about 60% to about 99% by weight, or from about 70% to about 99% by weight, or from about 80% to about 99% by weight, or from about 85% to about 99% by weight, or from about 90% to about 99% by weight.

Additionally, in certain embodiments, the accords comprise a least one, at least two, at least three, or at least four sulfur containing compounds. In certain embodiments, the accord can comprise at least one citrus compound and at least one sulfur containing compound. Alternatively or additionally, the accord can comprise at least one fruity compound and at least one sulfur containing compound.

In certain embodiments, the sulfur containing compound is selected from the group consisting of limonene thiol [CAS No. 68921-26-6], thiogeraniol ((2E)-3,7-dimethylocta-2,6-diene-1-thiol) [CAS No. 39067-80-6], RINGONOL® (8-mercapto-p-menthan-3-one) [CAS No. 38462-22-5] (e.g., the levo form of 8-mercapto-p-methan-3-one), oxane (e.g., 1,3-Oxathiane, 2-methyl-4-propyl-, cis-, [CAS No. 0059323-76-1]), p-menthene-8-thiol (i.e., grapefruit mercaptan or Corps 1490), and combinations thereof. The compounds here include constitutional isomers, enantiomers, stereoisomers and racemic mixtures of said compounds listed herein. Additional non-limiting examples of sulfur containing compounds include 4-methylthio-4-methyl-2-pentanone [CAS No. 23550-40-5], 3 mercapto-hexanol, methoxymethylbutanethiol, dibutyl sulfide, dimethyl sufide, thiocineol, 2-isopropyl-4-methylthiazole, and combinations thereof, and any other sulfur containing material compatible with a fragrance according including a citrus compound. In specific embodiments, the accord comprises thiogeraniol and rigonol. The compounds here include constitutional isomers, enantiomers, stereoisomers and racemic mixtures of said compounds listed herein.

In certain embodiments, the one or more sulfur containing compounds are present in a fragrance composition in amounts from about 0.000001% to about 0.5% by weight, or from about 0.00001% to about 0.25% by weight, or from about 0.00025% to about 0.125% by weight, or from about 0.005% to about 0.1% by weight. In certain embodiments, the one or more sulfur containing compounds are present in a fragrance composition in amounts of about 0.025% by weight. In certain embodiments, the fragrance composition comprises about 0.0001% limonene thiol, about 0.0003% thiogeraniol, about 0.01% RINGONOL®, and about 0.015% oxane by weight. In certain embodiments, the fragrance composition comprises from about 0.000001% to about 0.5% by weight, or from about 0.000001% to about 0.001%, from about 0.000005% to about 0.0005%, or from about 0.000005% to about 0.00025%, or from about 0.00001% to about 0.00025%, or from about 0.0001% to about 0.01% limonene thiol by weight. In certain embodiments, the fragrance composition comprises from about 0.000001% to about 0.5% by weight, or from about 0.000003% to about 0.003%, or from about 0.00002% to about 0.0015%, or from about 0.00002% to about 0.001%, or from about 0.00003% to about 0.001%, or from about 0.0003% to about 0.03% thiogeraniol by weight. In certain embodiments, the fragrance composition comprises from about 0.000001% to about 0.5% by weight, or from about 0.0001% to about 0.5%, or from about 0.0005% to about 0.01%, or from about 0.0005% to about 0.025%, or from about 0.001% to about 0.05%, or from about 0.01% to about 0.025% RINGONOL® by weight. In certain embodiments, the fragrance composition comprises from about 0.000001% to about 0.5% by weight, or from about 0.00015% to about 0.5%, or from about 0.001% to about 0.015%, or from about 0.001% to about 0.05%, or from about 0.0015% to about 0.075%, or from about 0.015% to about 0.5% oxane by weight.

In certain embodiments, one or more accords are formulated into a fragrance composition such that the fragrance composition includes from about 0.00001% to about 0.25%, or from about 0.0002% to about 0.025%, or from about 0.0005% to about 0.025% p-menthene-8-thiol by weight. In certain embodiments, a fragrance composition is formulated from one or more accords and includes two or more sulfur containing compounds. For example, in certain non-limiting embodiments, a fragrance composition comprises thiogeraniol and limonene thiol. In certain non-limiting embodiments, a fragrance composition comprises RINGONOL® and oxane. In certain embodiments, a fragrance composition comprises at least one of thiogeraniol, limonene thiol, RINGONOL®, oxane, and p-menthene-8-thiol, and further includes an additional sulfur containing compound.

In certain embodiments, the fragrance composition comprises an additional sulfur containing compound in an amount of from about 0.00001% to about 0.01% by weight. In certain embodiments, the additional sulfur containing compound is 4-methylthio-4-methyl-2-pentanone [CAS No. 23550-40-5]. For example, and not limitation, 4-methylthio-4-methyl-2-pentanone [CAS No. 23550-40-5] can be present in a fragrance composition in an amount from about 0.0002% to about 0.01% by weight. In certain embodiments, the additional sulfur containing compound is 3 mercaptohexanol. For example, and not limitation, 3 mercaptohexanol can be present in a fragrance composition in an amount from about 0.0002% to about 0.01% by weight. In certain embodiments, the additional sulfur containing compound is methoxymethylbutanethiol. For example, and not limitation, methoxymethylbutanethiol can be present in a fragrance composition in an amount from about 0.0001% to about 0.005% by weight. In certain embodiments, the additional sulfur containing compound is dibutyl sulfide. For example, and not limitation, dibutyl sulfide can be present in a fragrance composition in an amount from about 0.00002% to about 0.001% by weight. In certain embodiments, the additional sulfur containing compound is dimethyl sufide. For example, and not limitation, dimethyl sufide can be present in a fragrance composition in an amount from about 0.0001% to about 0.005% by weight. In certain embodiments, the additional sulfur containing compound is thiocineol. For example, and not limitation, thiocineol can be present in a fragrance composition in an amount from about 0.0002% to about 0.01% by weight. In certain embodiments, the additional sulfur containing compound is 2-isopropyl-4-methylthiazole. For example, and not limitation, 2-isopropyl-4-methylthiazole can be present in a fragrance composition in an amount from about 0.0001% to about 0.005% by weight.

In certain embodiments, the compositions also include one or more solvents or diluents. Such solvents or diluents include but are not limited to dowanols, isopars, and the like. Specific non-limiting examples include dipropylene glycol (DPG) (3-(3-hydroxypropoxy)propan-1-ol) [CAS Number: 25265-71-8], triethyl citrate (triethyl 2-hydroxypropane-1,2,3-tricarboxylate) [CAS Number: 77-93-0], and combinations thereof. Additional examples of solvents can include, but are not limited to, propylene glycol, dieth-phthalate (DEP), diisononyl phthalate (DINP), benzyl alcohol, dioctyl adipate, methyl hydrogenated rosinate [CAS No. 8050-15-5], terpenes (e.g., Glidsol 100), paraffinic naphthenic solvent (e.g., LPA-170 Solvent), isoalkanes (e.g., Soltrol 170 Isoparaffin), isoparaffins, isooctadecanol, (e.g., Tego Alkanol 66), phenoxyethanol, diethylene glycol monoethyl ether (Carbitol low gravity), glycol ether (Methyl Carbitol), Dipropylene Glycol Methyl Ether (e.g., Dowanol DPM), Dipropylene Glycol Methyl Ether Acetate (e.g., Dowanol DPMA), Propylene glycol methyl ether (e.g., Dowanol PM Glycol Ether), Tripropylene Glycol Methyl Ether, Diisoheptyl Phthalate (e.g., Jayflex® 77 available from Exxon), deionized or distilled water, specially denatured ethyl alcohol (e.g., SDA 40B), Dimethyl Adipate/Dimethyl Glutarate (e.g., DBE®-LVP Esters available from FLEXISOLV®), Racemic mixture (+/−)-2,2-dimethyl-4-hydroxymethyl-1,3-dioxolane (e.g., Augeo Clean Multi Solvent), Alcohol 40B Anhydrous 200 Proof, alcohol SDA 40B 190 Proof, Triacetin, 3-Methoxy-3-methyl-1-butanol (Solfit), Benzyl Laurate, Tripropylene Glycol Methyl Ether (e.g., Dowanol TPM), Dipropylene glycol n-butyl ether (e.g., Dowanol DPNB), Dimethyl siloxane, trimethylsiloxy-terminated (e.g., Dowanol Corning 200 Fluid), Caprylic/Capric Triglycerides (e.g., Neobee M-5), propylene glycol and glyceryl oleate (e.g., Arlacel 186), Uniceth-IC20L (e.g., Arlasolve 200 L), propanediol, 1,3, Butyl Cellosolve, Hexylene glycol, Glycerine, Isopropyl alcohol, 2-Methyl-1,3-propanediol (e.g., MP Diol Glycol), Diethyl Citrate, Triethyl Acetyl Citrate, Isopentyldiacetate (IPD-AC), Dimethyl 2-methylpentanedioate (e.g., Rhodiasolv Iris), medium chain triglycerides (MCT), terpene hydrocarbons (e.g., Dipentene 5100), 3,5,5-trimethylhexyl acetate, Diethyl Malonate, cyclohexyl acetate, para-tertiary-butyl (e.g., Vertenex), Diethyl Succinate, sunflower oil, soy bean methyl ester, benzyl benzoate, iso propyl myristate (IPM), Isopropyl palmitate (IPP/Deltyl Prime), butyl stearate, N Methyl Stearate, and combinations thereof.

In certain embodiments, the one or more solvents are present in an accord at an amount of from about 10% to about 70%, or from about 10% to about 50%, or from about 15% to about 40% by weight.

The amount of solvents used in a fragrance composition are less than about 70%, or less than about 60%, or less than about 50%, or less than about 40%, or less than about 30%, or less than about 20%, or less than about 10%, or less than about 5% of the total fragrance composition. In alternate embodiments, one or more solvents are present in a fragrance composition comprising one or more accords at an amount from about 1.5% to about 30.0% or from about 1.5% to about 26.0% by weight.

Additional solvents or diluents known in the art can also be used. The specific solvent used will depend on the particular end use product. The solvents can be used in amounts as needed, so long as the addition does not affect the overall fragrance note.

In certain embodiments, the fragrance compositions can comprise one or more accords and one or more additional fragrance compounds. In certain embodiments, the fragrance compositions can comprise two or more accords and one or more additional fragrance compounds. In certain embodiments, the fragrance compositions can comprise three or more accords and one or more additional fragrance compounds. In certain embodiments, the additional fragrance compounds in the accord constitute less than about 50%, or less than about 25%, by weight.

In certain embodiments, one or more citrus compounds are present in a fragrance composition comprising one or more accords at an amount from about 0.0001% to about 100%, or from about 0.0001% to about 80%, 0.0003% to about 65% or from about 0.0003% to about 40% by weight. In certain embodiments, one or more herbal/aromatic compounds are present in a fragrance composition comprising one or more accords at an amount from about 0.1% to about 80%, or from about 0.1% to about 50%, or from about 0.1% to about 10% or from about 0.1% to about 7% by weight. In certain embodiments, one or more fruity compounds are present in a fragrance composition comprising one or more accords at an amount from about 0.0001% to about 100%, or from about 0.0001% to about 25%, or from about 0.0003% to about 2.0% or from about 0.0003% to about 1.5% by weight.

In one aspect, a fragrance composition for eliciting a consumer's perception of hygiene comprising at least one fragrance accord, wherein said fragrance accord comprises (i) two or more sulfur containing components; and (ii) at least one additional component selected from the group consisting of a citrus component, herbal component, fruity component, and combinations thereof is disclosed.

A fragrance composition comprising: aldehyde c-12 lauric; decenal, cis-4; decenal, trans-2; mandarin aldehyde 10% TEC; Cymene, P; Lemon Oil Terpenes White; Limonene Thiol 1% TEC 10% TEC; Orange Oil Pera Brazil; Orange Oil Terpenes White; Oxane 969380/TEC 50%; Rhubafuran; RINGONOL® 50 TEC; Terpinolene 20; Thiogeraniol; Thymol Crystals; Citronellyl Acetate; Dimethyl Anthranilate; Eugenol; Indole Crystal; Methyl Anthranilate, Meth Jasmonate; *Perilla* Aldehyde; Phellandrene, Alpha; Linalool Syn; Dynascone Neat 939.745; *Galbanum* Oil A Nat; Hexen-1-Ol, Cis-3; Hexenal, trans-2; *Perilla* Ald; Phellandrene, Alpha; Linalool Syn; and Triethyl Citrate is disclosed.

A fragrance composition comprising: Cymene, P; decenal, cis-4 @ 10% in DPG; decenal, trans-2, @ 1% in DPG; dipropylene glycol; Dynascone Neat 939.745 @ 10% in DPG; Eugenol @ 10% in DPG; *Galbanum* Oil A Nat @ 1% in DPG; Hexen-1-ol, Cis-3; Hexenal, trans-2 @ 10% in DPG; Limonene Thiol 1% TEC 10% TEC; Linalool Syn; mandarin aldehyde 10% TEC; Orange Pera Brazil Nat EO; Oxane 969380 @ 10% in TEC; *Perilla* Aldehyde; Rhubafuran @ 10% in DPG; RINGONOL® 50 @ 10% in TEC; Thiogeraniol @ 0.1% in TEC; and Thymol Crystals is disclosed.

A fragrance composition comprising: aldehyde c-12 lauric @ 10% in DPG; decenal, cis-4 @ 10% in DPG; decenal, trans-2 @ 1% in DPG; dimeth anth; dipropylene glycol; Dynascone Neat 939.745; *Galbanum* Nat EO @ 1% in DPG; Hexen-1-ol, Cis-3; Hexenal, trans-2, @ 10% in DPG; Indole Crystal @ 0.1% in DPG; Linalool Syn; mandarin aldehyde 10% TEC; Methyl Anthranilate @ 1% in DPG; Meth Jasmonate @ 10% in DPG; Oxane 969380 @ 10% in DPG; *Perilla* Aldehyde; Phellandrene, Alpha; Rhubafuran @ 10% in DPG; RINGONOL® 50 @ 10% in TEC; Terpinolene 20; Thiogeraniol @ 0.1% in TEC; and Thymol Crystals is disclosed.

A fragrance composition comprising: Cymene, P; decenal, cis-4 @ 10% in DPG; decenal, trans-2, @ 1% in DPG; dipropylene glycol; Dynascone Neat 939.745 @ 10% in DPG; Eugenol @ 10% in DPG; *Galbanum* Nat EO @ 1% in DPG; Hexen-1-01, Cis-3; Hexenal, trans-2, @ 10% in DPG; Limonene Thiol 1% TEC 10% TEC; Linalool Syn; mandarin aldehyde 10% TEC; Orange Pera Brazil Nat EO; Orange White Terpenes Nat EO; Oxane 969380 @ 10% in TEC; *Perilla* Aldehyde; Phellandrene, Alpha; Rhubafuran @ 10% in DPG; RINGONOL® 50 @ 10% in TEC; Terpinolene 20; Thiogeraniol @ 0.1% in TEC; and Thymol Crystals is disclosed.

A fragrance composition comprising: aldehyde c-12 lauric @ 10% in DPG; citronellyl acetate; Cymene, P; decenal, cis-4 @ 10% in DPG; decenal, trans-2 @ 1% in DPG; dimeth anth; dipropylene glycol; Dynascone Neat 939.745 @ 10% in DPG; Eugenol @ 10% in DPG; *Galbanum* Nat EO @ 1% in DPG; Hexen-1-Ol, Cis-3; Hexenal, trans-2, @ 10% in DPG; Indole cryst @ 0.1% in DPG; Limonene Thiol 1% TEC 10% TEC; Linalool Syn; mandarin aldehyde 10% TEC; meth jasmonate @ 10% in DPG; Orange Pera Brazil Nat EO; Orange White Terpenes Nat EO; Oxane 969380 @ 10% in TEC; *Perilla* Aldehyde; Phellandrene, Alpha; Rhubafuran @ 10% in DPG; RINGONOL® 50 @ 10% in TEC; Thiogeraniol @ 0.1% in TEC; and Thymol Crystals is disclosed.

3. Use of Compositions in Consumer Products

The presently disclosed fragrance formulas are exemplary. To one skilled-in-the-art of fragrance creation, a formula may be optimized for performance contingent on the specific product category and/or formulation type (e.g., stability, substantivity, diffusivity). In addition, one may further optimize the appropriate fragrance usage level in the consumer product by correlating the hedonic and psychophysical responses via a fragrance dose-response curve.

In certain embodiments, the fragrance compositions and accords of the present disclosure are formulated as part of a consumer product. In certain embodiments, the fragrance composition comprises one or more of the accords of the present disclosure.

In certain embodiments, the consumer products of the present disclosure can be, but are not limited to, household or home care products. Non-limiting examples of such products include air care products (e.g., candles, aerosols, spray devices, air fresheners, liquid electric air fresheners, fragrance diffusers, gel air fresheners, wick air fresheners, reservoir air fresheners, porous membrane air fresheners, power assisted delivery air fresheners, including thermal drop-on-demand air fresheners, piezo air fresheners, heater air fresheners, fan air fresheners, and microfluidic devices air fresheners, etc.); home cleaning products (e.g., hand and auto dish cleaners, hard surface cleaners, laundry products such as laundry detergents, softeners, cleaners, dryer sheets, etc.); personal care products (e.g., lotions, creams, body washes, hand soaps, shampoos, conditioners, soaps, clothing, etc.); baby care products (e.g., consumer products relating to disposable absorbent and/or non-absorbent articles, including adult incontinence garments, bibs, diapers, training pants, infant and toddler care wipes); fabric and home care products (e.g., consumer products for fabric conditioning (including softening), laundry detergency, laundry and rinse additive and/or care, dryer sheets, perfume beads, air care, car care, dishwashing, hard surface cleaning and/or treatment, and other cleaning for consumer and or institutional use, etc.); bathroom cleaning products (e.g., bath or tile cleaner, toilet cleaner, sink cleaner, disinfectants, antimicrobial products, mildew cleaners, etc.); sanitary products (e.g., towels, toilet paper, tissue paper, wet tissue paper, handkerchiefs, wet towels, etc.); family care products (e.g., wet or dry bath tissue, facial tissue, disposable handkerchiefs, disposable towels, and/or wipes, towels, toilet paper, tissue paper, wet towels, etc.); feminine care products (e.g., catamenial pads, incontinence pads, interlabial pads, panty liners, pessaries, sanitary napkins, tampons and tampon applicators, and/or wipes, etc.); sexual health care products (e.g., products relating to sexual aids or sexual health, including lubricants and condoms, etc.); pet care products (e.g., pet malodor cat litter, litter boxes, pet deodorizers, pet health and nutrition including pet foods, treats, other orally deliverable products, grooming aids, products for treating pet hair/fur including shampooing, styling, conditioning; deodorants and antiperspirants; products for cleansing or treating pet skin, including soaps, creams, lotions, and other topically applied products; training aids, toys and diagnostics techniques); fine fragrance (including hydro alcoholic solutions of perfume oil, such as parfum/extrait de parfum, eau de parfum/millesime/parfum de toilette, eau de toilette, eau de cologne, body splash, after shave, body mists, including baby colognes); auto care products (e.g., cleaners, air fresheners, wipes, soaps, etc.); cosmetics (e.g., skin cream, cleansing cream, night cream, hand cream, lotion, after-shave lotion, body lotion, foundation, lip stick, lip cream, nail polish, nail polish remover, talcum powder, anti-wrinkle and/or anti-aging cosmetics, sun protection products, massage oil, etc.); beauty care (e.g., products for treating human hair including shampooing, styling, conditioning; deodorants and antiperspirants; products for personal cleansing; products for treating human skin, including application of creams, lotions, and other topically applied products; products for shaving, rinse, rinse in shampoo; hair styling agents such as pomade, hair tonic, hair gel, hair cream and hair mousse; hair growing agents; hair coloring agents; etc.); and bath agents (e.g., powder bath additives, solid foaming bath additives, bath oils, bubble bath aroma generators, bath salts, etc.); hair removal products (e.g., products for hair removal including depilatory creams, sugar pastes or gels, waxes); writing products (e.g., pens, crayons, paints, pencils, paper, origami, seals, etc.); products for play (e.g., balls, beanbags, cards, tops, dolls, building blocks, etc.); pharmaceuticals (e.g., plasters, ointments, lotions, etc.); flavored products (e.g., confections, beverages, gum, etc.); pharmaceuticals (e.g., plasters, ointments, suppositories, tablets, liquid medicines, capsules, granules, pharmacologically active molecular and/or biological entities; their use in the treatment and/or prevention of diseases and/or alleviation of symptoms in humans and/or animals, and formulations, regimens, kits and/or routes of delivering such entities to subjects in need of treatment and/or prevention and/or alleviation, etc.); health care products (e.g., oral health care products, including any composition for use with any soft and/or hard tissue of the oral cavity or conditions associated therewith (e.g., tooth paste, oral wash, mouth rinse, mouthwash, anti-cavities compositions, anti-plaque chewing gum compositions, breath compositions, dentrifices, denture compositions, lozenges, rinses, and tooth whitening compositions), cleaning devices, floss and flossing devices and toothbrushes; over-the-counter health care including cough and cold remedies and treatments for other respiratory conditions, pain relievers whether topical, oral, or otherwise, gastrointestinal remedies including any composition suitable for the alleviation of gastrointestinal conditions such as heartburn, upset stomach, diarrhea, and irritable bowel syndrome, and nutrient supplementation such as calcium or fiber supplementation, etc.); and foods and drinks or beverages.

In certain embodiments, the disclosed subject matter provides for use of the fragrance compositions and/or accords described herein in a consumer product or consumer product base as described herein.

In certain embodiments, the fragrance compositions and/or accords are formulated as part of a product, which stimulates perception of hygiene, of leaving surfaces free of bacteria or microbes.

In certain embodiments, the fragrance compositions and/or accords are formulated as part of a product, which stimulates perceptions of cleanliness, of freshness, of removing tough food, grease, dirt and/or grime, and/or leaving surfaces clear and/or shining.

In certain embodiments, the fragrance compositions and/or accords are formulated as part of a product, which stimulates perception of pride or proudness with a particular space.

In specific embodiments, the subject disclosure relates to methods of incorporating a fragrance, which stimulates the perception of hygiene into a consumer product. In certain embodiments, methods include a) providing at least one consumer product or consumer product base, and b) combining the consumer product or consumer product base with a fragrance composition comprising at least one, two, three or more accords.

The concentration and/or amount of the composition admixed with the consumer product or consumer product base to stimulate the perception of hygiene in a consumer can change based on a number of variables, for example, the specific consumer product, the physical form of the consumer product (e.g., liquid, gas, or solid) and what fragrance compounds are already present in the consumer product and the concentrations and/or amounts thereof.

A broad range of concentrations and/or amounts of the fragrance composition and/or accord can be employed to stimulate the perception of hygiene in a consumer. In certain embodiments of the present disclosure, the fragrance composition and/or accord is admixed with a consumer product or consumer product base, and the fragrance composition is present in the consumer product or consumer product base in a concentration and/or amount as required based on the form of the product, e.g., liquid, solid, aerosol, spray, etc.

In certain embodiments of the present disclosure, the fragrance composition and/or accord is admixed with a consumer product, wherein the composition is present in an amount from about 0.0001% to about 99% weight/weight (w/w), or from about 0.001% to about 75% w/w, or from about 1% to about 60% w/w, or from about 5% to about 50% w/w, or from about 10% to about 40% w/w, and values in between.

In certain products, by way of nonlimiting example, the fragrance composition in an air freshener (e.g., membrane or liquid electric) may contain about 100% fragrance composition. In such instances, the one or more accords of the presently disclosed subject matter can make up to about 100% of the fragrance composition.

In other nonlimiting examples, where the consumer product is, e.g., a candle or concentrated aerosol, the one or more accords of the presently disclosed subject matter can make up less than about 15%, or less than about 10%, of the consumer product composition. Where the consumer product is, e.g., a laundry, APC, or personal care product, the one or more accords of the presently disclosed subject matter can make up less than about 10%, or less than about 5%, of the consumer product composition.

In certain embodiments of the present disclosure, the amount of the fragrance composition and/or accord released from the consumer product during use is less than the total amount of the composition and/or accord admixed with the consumer product. In certain embodiments, the amount of the composition and/or accord released by the consumer product, and therefore available for administration to the subject, is between about 1 and 100% of the amount of fragrance composition and/or accord admixed with the consumer product. In further embodiments, the amount of fragrance composition and/or accord released is between about 5 and 90%, between about 10 and 80%, between about 20 and 70%, between about 30 and 60%, and between about 40 and 50% of the amount of fragrance composition and/or accord admixed with the consumer product.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

4. Perception of Hygiene

The accords and compositions of the presently disclosed subject matter are administered in an amount effective to stimulate the perception of hygiene in a consumer.

In certain embodiments, the perception of hygiene along with pleasantness is measured by various consumer testing procedures, including but not limited to Central Location Tests (CLT) involving directed smelling of the odors (sniff tests) and ratings on numerical scales using generally accepted industry standards, Cross Modal Tests of the effects of odors on the perception of images drawn from relevant usage moments for hygiene-related products (e.g., kitchen(s) and/or bathroom(s)), and Home Use Testing (HUT). Different considered and conscious perceptions or senses can be queried in this regard. In certain embodiments, a control or blank is used before or after the administration of a test sample. Non-limiting examples of a negative control include air or a blank and the absence of any fragrance. Non-limiting examples of a positive control include a widely available natural odorant with nearly universal association with hygiene but which is considered singular, recognizable, harsh, relatively less pleasant, or some combination thereof. In certain embodiments, the CLT comprises each consumer sniffing a set number of accords or finished fragrances and then rating the fragrance. In certain embodiments, the order of the accords of fragrances may be rotated for each consumer. For example, a consumer sniffs the sample and then describes whether they perceived a certain characteristic, i.e., hygiene, in connection with the sample. One or more control sample can be included in the rotation of test samples. In certain embodiments, the consumer is the female head of household and responsible for the housework in the home.

In other embodiments, the perception of hygiene is measured through Home Use Testing (HUT) using generally accepted industry standards. In certain embodiments, the home use test indicates a consumer's considered or overall summation of their perception of liking/pleasantness and as well their overall likelihood to purchase the tested consumer product in the future, along with considered and conscious reasons for said overall perceptions which may include the perception of cleaning and hygiene as assessed based on recollection of using the test products in the consumer's own home. One or more control sample can be included in the overall design of the test In certain embodiments, the consumer is the head of household and responsible for the housework in the home.

In certain other embodiments, the perception of hygiene is measured through Cross-Modal testing, which is described generally in Knoeferle et al., Psychology and Marketing, 32:107-120 (2015), the disclosure of which is incorporated herein by reference. Specifically, the perception of hygiene is measured through indirect means that capture rapidly formed judgments and pre-conscious or sub-conscious impressions across two or more sensory modes, such as olfaction and vision. In these methods the consumer is not asked to directly evaluate the product or fragrance as an odor. For example, consumers judge images of relevant consumer home conditions as the primary stimulus (i.e., a bathroom, a kitchen, a bedroom, etc.). The consumer is then exposed to a series of odors in rapid succession timed vs. inhalation. The consumer can be exposed to a control, or blank, between each odor of the series, or as a targeted odor, or both. Upon exposure to a specific odor, the consumer scores the images on a numerical scale for different attributes. The effect of the odor or fragrance on the consumer's visual perception is studied.

It is noted that one of the key distinctions between CLT and HUT testing as compared to Cross-Modal testing, is that overall liking, pleasantness and likelihood of future purchase or purchase intent are generally assessed in CLT and HUT. However, these are not assessed in cross-modal testing, unless added to the end of a Cross-Modal experiment. A purchase intent response requires considerable time and cognition to form, whereas hygienic perception can be formed nearly immediately and evolved continuously over time. For pleasant fragrances, in a traditional CLT or HUT, it is well known that consumers who indicate high scores for overall purchase intent of a product, when asked about other specific attributes afterwards, tend to maintain those high scores simply because it makes sense to continue to respond this way, or because they are in a better mood at that moment (e.g. "I said I liked this dish soap, so therefore I really ought to say it did a good job at cleaning, killing germs, etc.). These effects are known as "hedonic haloing" and "confirmation bias". Cross-Modal provides additional support that hygiene perception is not due merely to post-rationalization or haloing on the part of consumers.

EXAMPLES

The presently disclosed subject matter will be better understood by reference to the following Examples, which are provided as exemplary of the disclosure, and not by way of limitation.

Example 1: Hygiene Fragrance Composition and Accords A-D

Example 1 provides a fragrance composition in accordance with the presently disclosed subject matter.

TABLE 1

| Name | CAS No. | IUPAC Name | Parts/weight |
|---|---|---|---|
| ALDEHYDE C-12 LAURIC | 112-54-9 | Dodecanal | 0.300 |
| DECENAL, CIS-4 | 21662-09-9 | (Z)-dec-4-enal | 0.200 |
| DECENAL, TRANS-2, | 3913-81-3 | (E)-dec-2-enal | 0.020 |
| MANDARIN ALD 10% TEC | 20407-84-5 | trans-2-Dodecenal | 2.000 |
| CYMENE, PARA, | 99-87-6 | 1-methyl-4-propan-2-ylbenzene | 15.000 |
| LEMON OIL TERPENES WHITE | 68917-33-9 | N/A | 7.000 |
| LIMONENE THIOL 1% TEC 10% TEC | 68921-26-6 | N/A | 1.000 |
| LINALOOL OXIDE | 1365-19-1 11063-76-6 | 2-(5-methyl-5-vinyltetrahydro-2-furanyl)-2-propanol | 0.070 |
| ORANGE OIL PERA BRAZIL | 8008-57-9 | N/A | 400.000 |
| ORANGE OIL TERPENES WHITE | 8028-48-6 | N/A | 200.000 |
| OXANE 969380/TEC 50% | 0059323-76-1 | 1,3-Oxathiane, 2-methyl-4-propyl-, cis- | 0.300 |
| RHUBAFURAN | 82461-14-1 | 2,4-dimethyl-4-phenyloxolane | 0.300 |
| RINGONOL ® 50 TEC | 38462-22-5 | mercaptomenthone-8 | 0.200 |
| TERPINOLENE 20 | 586-62-9 | 1-methyl-4-propan-2-ylidenecyclohexene | 3.500 |
| THIOGERANIOL | 39067-80-6 | (2E)-3,7-dimethylocta-2,6-diene-1-thiol | 0.003 |
| THYMOL CRYSTALS | 89-83-8 | 5-methyl-2-propan-2-ylphenol | 4.000 |
| CITRONELLYL ACETATE | 150-84-5 | 3,7-dimethyloct-6-enyl acetate | 1.500 |
| DIMETHYL ANTHRANILATE | 85-91-6 | methyl 2-methylaminobenzoate | 7.000 |
| EUGENOL | 97-53-0 | 2-Methoxy-4-(2-propen-1-yl)-phenol | 0.150 |
| INDOLE CRYSTALS | 120-72-9 | 1H-indole | 0.002 |
| METHYL ANTHRANILATE | 134-20-3 | Benzoic acid, 2-amino-, methyl ester | 0.007 |
| METHYL JASMONATE | 39924-52-2 | methyl 2-(3-oxo-2-pent-2-enylcyclopentyl)acetate | 0.200 |
| DYNASCONE NEAT 939.745 | 23696-85-7 | 1-(2,6,6-Trimethyl-1,3-cyclohexadien-1-yl)-2-butene-1-one | 0.150 |
| GALBANUM OIL A NAT | 8023-91-4 | *ferula galbaniflua* resin oil | 0.003 |
| HEXEN-1-OL, CIS-3, | 928-96-1 95123-47-0 | (Z)-hex-3-en-1-ol | 15.000 |
| HEXENAL, TRANS-2, | 6728-26-3 | (E)-hex-2-enal | 0.200 |
| PERILLA ALDEHYDE | 2111-75-3 | 4-prop-1-en-2-ylcyclohexene-1-carbaldehyde | 2.000 |
| PHELLANDRENE, ALPHA | 99-83-2 | 2-methyl-5-propan-2-ylcyclohexa-1,3-diene | 1.000 |
| LINALOOL SYN | 78-70-6 11024-20-7 | 3,7-Dimethyl-1,6-octadiene-3-ol | 70.000 |
| DIPROPYLENE GLYCOL | 25265-71-8 | 3-(3-hydroxypropoxy)propan-1-ol | 252.398 |
| TRIETHYL CITRATE | 77-93-0 | triethyl 2-hydroxypropane-1,2,3-tricarboxylate | 16.497 |
| Total WO Dilutions | | | 731.105 |
| Total | | | 1000.000 |

The above hygiene composition provides perception of hygiene when used in consumer products.

The hygiene composition was further investigated, and it was discovered that at least four separate accords (Accords A-D) could be formulated from the hygiene composition. These accords are described in Table 2.

TABLE 2

Accord compositions in units of percent quantity of total.

| | ACCORD A | ACCORD B | ACCORD C | ACCORD D |
|---|---|---|---|---|
| ALDEHYDE C-12 LAURIC @ 10% IN DPG | | 1.5 | | 2.5 |
| CITRONELLYL ACETATE | | | | 7.5 |
| CYMENE, PARA, | 3.75 | | 3.846 | 1.25 |
| DECENAL, CIS-4 @ 10% IN DPG | 0.5 | 1 | 0.513 | 1 |
| DECENAL, TRANS-2, @ 1% IN DPG | 0.5 | 1 | 1.026 | 1 |
| DIMETHYL ANTHRANILATE | | 3.5 | | 1.5 |
| DIPROPYLENE GLYCOL | 17 | 30 | 26.41 | 40.5 |
| DYNASCONE NEAT 939.745 @ 10% IN DPG | 0.375 | 0.75 | 0.513 | 0.25 |
| EUGENOL @ 10% IN DPG | 0.375 | | 1.282 | 2.5 |
| GALBANUM NAT EO @ 1% IN DPG | 0.75 | 1.5 | 5.128 | 2.5 |
| HEXEN-1-OL, CIS-3, | 3.75 | 7.5 | 3.846 | 1 |
| HEXENAL, TRANS-2, @ 10% IN DPG | 0.5 | 1 | 0.513 | 0.5 |
| INDOLE CRYSTALS @ 0.1% IN DPG | | 1 | | 1 |
| LIMONENE THIOL 1% TEC @ 10% TEC | 0.25 | | 0.256 | 0.25 |
| LINALOOL SYN | 17.5 | 35 | 25.641 | 20 |
| MANDARIN ALDEHDYE 10% TEC | 0.5 | 1 | 0.256 | 0.5 |
| METHYL ANTHRANILATE @ 0.1% IN DPG | | 3.5 | | |
| METHYL JASMONATE @ 10% IN DPG | | 1 | | 0.5 |
| ORANGE PERA BRAZIL NAT EO | 50 | | 12.821 | 5 |
| ORANGE WHITE TERPENES NAT EO | | | 12.821 | 7.5 |
| OXANE 969380 @ 10% IN TEC | 0.75 | 1.5 | 0.513 | 0.5 |
| PERILLA ALDEHYDE | 0.5 | 1 | 0.256 | 0.25 |
| PHELLANDRENE, ALPHA | | 0.5 | 0.513 | 0.25 |
| RHUBAFURAN @ 10% IN DPG | 0.75 | 1.5 | 0.513 | 0.5 |
| RINGONOL ® 50 @ 10% IN TEC | 0.5 | 1 | 0.513 | 0.5 |
| TERPINOLENE 20 | | 1.75 | 1.026 | |
| THIOGERANIOL @ 0.1% IN TEC | 0.75 | 1.5 | 0.769 | 0.75 |
| THYMOL CRYSTALS | 1 | 2 | 1.026 | 0.5 |

The accords can also be used alone and/or in combination with consumer products to provide perception of hygiene in a consumer.

Example 2: Hygiene Fragrances Formulations

Example 2 provides the compositions of fragrance compositions (Fragrances 1-6) which comprise each of Accords A-D as described in Example 1 and an additional fragrance (Fragrance F). The additional fragrance can be described as a Floral-Green-Fruity accord.

The compositions are formulated as described in Table 3.

TABLE 3

Fragrances 1-6.

| | |
|---|---|
| Fragrance 1: | 0.5% dipropylene glycol; Accord A and Fragrance F in a ratio of 6:4. |
| Fragrance 2: | 0.5% dipropylene glycol; Accord B and Fragrance F in a ratio of 8:2. |
| Fragrance 3: | 0.5% dipropylene glycol; Accord C and Fragrance F in a ratio of 7:3. |
| Fragrance 4: | 0.5% dipropylene glycol; Accord D and Fragrance F in a ratio of 6:4. |
| Fragrance 5: | 0.8% dipropylene glycol; Accord A and Fragrance F in a ratio of 6:4. |
| Fragrance 6: | 0.5% dipropylene glycol; Fragrance F (control). |

Example 3: Consumer Products Containing Hygiene Fragrances

Example 3 provides non-limiting formulation examples of consumer products containing hygiene fragrances. The hygiene composition of Example 1 or one or more of the accords of Example 1 can be used to create the hygiene composition in the following tables.

Table 4 provides a formulation for a hard surface cleaner pump spray. In a suitable vessel, the different ingredients are mixed until completely uniform and clear. With constant agitation, water is slowly added to the clear solution. Preservative is added with stirring after the water. The formulation can then be filled into suitable containers.

TABLE 4

| Ingredient | Percentage | Purpose |
|---|---|---|
| Neodol 91-8 | 4.0 | Surfactant |
| Dowanol DPnB | 4.0 | Solvent |
| Hygiene Composition | 1.0 | Fragrance |
| Kathon CG | 0.07 | Preservative |
| D.I. Water | 90.93 | Solvent |

Table 5 provides a formulation for a water-based aerosol air freshener. This product is considered a 3-stage fill. The mixing is not complete until the aerosol formulation is complete in the container. In a suitable vessel, the Witconol and fragrance is mixed until completely uniform and clear. Separately, the sodium nitrite is dissolved in the water. The formulation is then filled into aerosol cans as separate phases. The fragrance phase is filled first. The water phase is filled second. The can is then crimped and the propellant is pressure filled through the valve. The can is then shaken to complete the W/O emulsion. This formulation meets the VOC requirements of 30% VOCs for aerosol air fresheners. The can should be an epoxy-lined tinplate can. The valve used on this product must be specified for a water-based, fine spray and with a vapor tap. While there are many suitable combinations, an 0.018 stem with an 0.050 capillary dip tube and an 0.013 vapor tap is acceptable. A mechanical break-up actuator with an 0.018 orifice or spray-thru overcap will provide an acceptable spray.

TABLE 5

| Ingredient | Percentage | Purpose |
|---|---|---|
| Witconol 14 | 1.00 | w/o Frag Emulsifier |
| Hygiene Composition | 0.50 | Fragrance |
| D. I. Water | 69.45 | Solvent |
| Sodium Nitrite | 0.05 | Corrosion Inhibitor |

TABLE 5-continued

| Ingredient | Percentage | Purpose |
| --- | --- | --- |
| Hydrocarbon Propellant A-46 | 29.00 | Propellant |

Table 6 provides a formulation for a liquid laundry detergent. Water is heated to 65° C. Glucopon is added and is mixed at medium speed until clear. Standapol is added and is mixed until clear and homogenous. The mixture is removed from heat, and the remaining ingredients are added in order, mixing at slow to medium speed for each addition. pH is adjusted with sulfuric acid solution to pH of 8.0 to 8.5. Viscosity is adjusted with sodium chloride.

TABLE 6

| Ingredient | INCI | Percentage |
| --- | --- | --- |
| Water | Water | Q.S. |
| Glucopon 625UP (1) | Alkyl Polyglucosides | 12.50 |
| Standapol ES-40 (1) | Alkyl Ether Sulfates | 25.60 |
| Versene 100 (38%) (2) | Tetrasodium EDTA | 00.40 |
| MEA (2) | Monoethanolamine | 01.00 |
| Sulfuric Acid (25% Aq.) | Acid | 03.00 |
| Sodium Chloride (25%) | Salt | 01.20 |
| Hygiene composition | Fragrance | 00.75 |

Table 7 provides a formulation for a fabric deodorizer. In a suitable vessel, Alcohol SD-40B, Tergitol, DPG, PG and fragrance are mixed until completely uniform and clear. With constant agitation, water is slowly added to the solution. With agitation, Kathon is added. The final formulation should be clear. The formulation can be then filled into suitable plastic containers (PET preferred), with the proper trigger or pump closure.

TABLE 7

| Ingredient | Percentage | Purpose |
| --- | --- | --- |
| Tergitol 15-S-9 | 15.00 | Emulsifier |
| DPG | 12.00 | Solvent |
| Propylene Glycol | 6.00 | Solvent |
| Alcohol SD 40B | 6.00 | Solvent |
| Hygiene Composition | 5.00 | Fragrance |
| D. I. Water | 55.92 | Solvent |
| Kathon CG | 0.08 | Preservative |

Table 8 provides a formulation for a clear liquid hand soap. DI water is heated to 65° C. and Methyl Paraben is slowly added, mixing together at medium/high speed using an overhead mixer until completely into solution and clear (Seq. #1). Seq. #2 is added to Seq. #1 at low speed until completely clear. Seq. #3 is added to batch without heating, in order of addition, and cooled down to 35° C. with low agitation. Seq. #4 is premixed until clear, and added to batch. Seq. #5 is added to batch with low agitation, cooling down to 25° C. Seq. #6 is added to adjust batch to desired pH. The product is jarred up, pouring very slowly onto the sides of the jars to eliminate any additional aeration.

TABLE 8

| SEQ. | INGREDIENTS | INCI | PERCENT |
| --- | --- | --- | --- |
| 1 | Deionized water | Water | 66.50 |
| 1 | Methyl Paraben | (1) Methyl Paraben | 00.25 |
| 2 | Liponic EG-1 | (2) Glycereth-26 | 01.00 |
| 2 | Glycerin | (3) Glycerin | 01.00 |
| 2 | Lipopeg 6000DS | (2) PEG-150 Distearate | 00.50 |
| 3 | Monamid 716 | (4) Lauramide DEA | 03.50 |
| 3 | Standapol ES-2 | (3) Sodium Laureth Sulfate | 25.00 |
| 3 | Velvetex BK-35 | (3) Cocamidopropyl Betaine | 15.00 |
| 4 | Deionized Water | Water | 01.00 |
| 4 | Unicide U-13 | (2) Imidazolidinyl Urea | 00.25 |
| 5 | Hygiene Composition | | 00.50 |
| 6 | Citric acid (25% Sol'n) | | QS |

Table 9 provides a formulation for auto dish wash detergent. In a suitable vessel, TKPP and Kasil 1 is dissolved in water until uniform. The remainder of the ingredients are slowly added in the order given with constant agitation. The formulation should be a clear liquid.

TABLE 9

| Ingredient | Percentage |
| --- | --- |
| TKPP Tetrapotassium Pyrophosphate, 60% | 33.30 |
| KASIL 1 Potassium Silicate | 20.00 |
| Sodium Hypochlorite (15%) | 8.00 |
| Bio-terge PAS-8S | 3.00 |
| Sodium Hydroxide 50% solution | 1.00 |
| Hygiene Composition | 0.50 |
| D. I. Water | q.s. |

The appearance of the detergent is clear liquid. The pH is 12.0. This detergent has low viscosity and can be used in dishwashing machines at a concentration of 2 to 4 oz/gal.

Example 4: Testing of Odorants with Photographs

Example 4 provides the results from a Cross-Modal study that tested the compositions of the presently disclosed subject matter.

30 female participants ranging in ages 21 to 55 were included in this study. The participants were also the primary dish washer in their homes. Each participant was shown various photographs of home kitchens, and each participant was rapidly exposed to a series of odors (separated by air). Upon exposure to a specific image-odor combination, the participants scored the photographs on a 9-point scale for different hygiene-related attributes.

Figure 2:
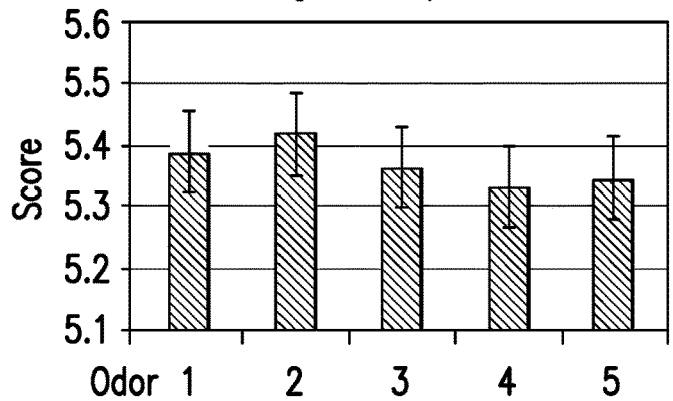
FIG. 2 depicts the average attribute score for perceived germ kill as perceived based on kitchen images in the presence of the different odors of Example 4.
Figure 3:
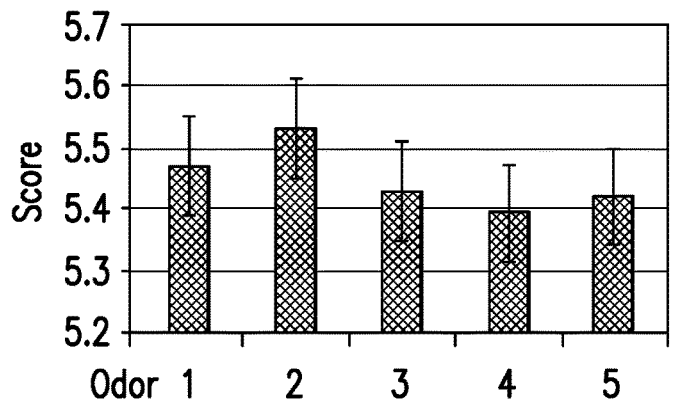
FIG. 3 depicts the average attribute score for perceived cleanliness as perceived based on kitchen images in the presence of the different odors of Example 4.

There were five test odors (#1-#5). Odor 1 was a hygiene composition with a fougere fragrance. Odor 2 was a hygiene composition with a citrus fragrance. Odor 3 was a hygiene composition with a citrus green fragrance. Odor 4 was a lemon oil control fragrance. Odor 5 was simply air. There were three hygiene-related perceptual attributes that were assessed for each image and odor combination: germ removal, germ kill and clean. Results of the scoring are shown in FIGS. 1-3.

Figure 4:
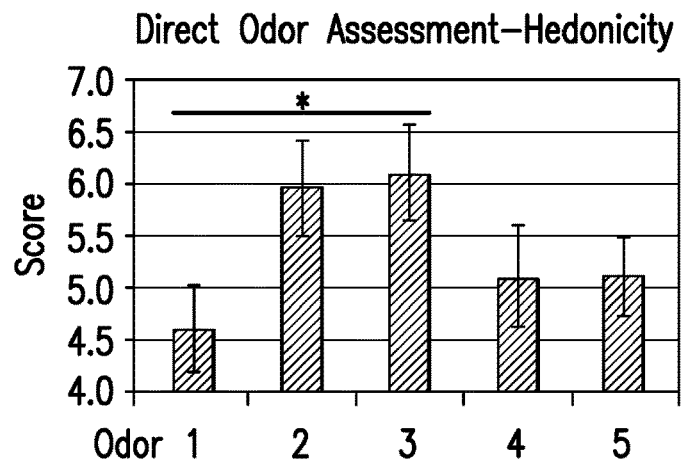
FIG. 4 depicts the average direct odor assessment scores for hedonicity of the different odors of Example 4.
Figure 5:
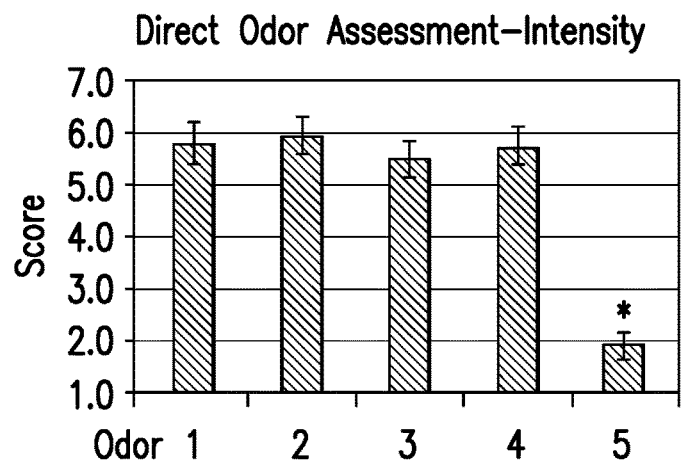
FIG. 5 depicts the average direct odor assessment scores for intensity of the different odors of Example 4.
Figure 6:
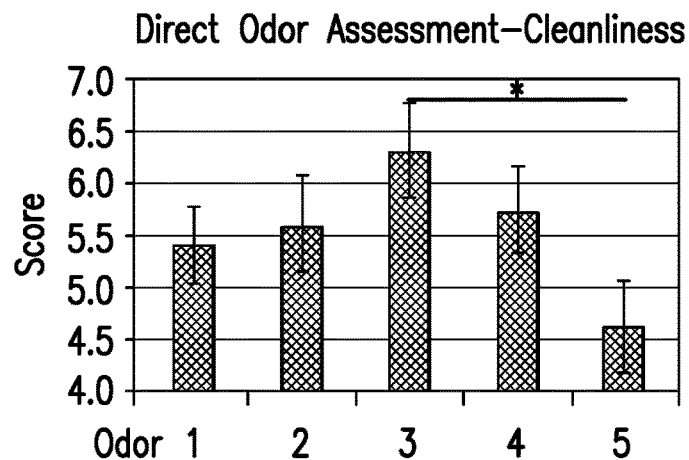
FIG. 6 depicts the average direct odor assessment scores for cleanliness of the different odors of Example 4.

At the conclusion of the Cross-Modal experiment, participants were then asked to directly assess and self-report on the odors based on their impressions of hedonicity, intensity, and cleanliness of each odor on the same scale. Results of the self-reporting are shown in FIGS. 4-6.

The results showed that Odor 2 had the highest score for all attributes. Odor 3 had the best overall self-reporting scores. Perceived germ kill assessments were lower than perceived germ removal.

Example 5: Impact of Odors on Varying Attributes

Example 5 demonstrates how different specific odors affect different measurable hygiene-related attributes via a Cross-Modal study. Participants were shown photographs of home kitchens and home bathrooms (including bathroom surfaces and toilets). Participants were exposed to the different odors and were asked to assess attributes on a numerical scale. The different odors were floral, citrus, aromatic, fougere, rosemary and control air. The different attributes measured were hygienic, clean, and proud/pleasing (to invite friends).

Figure 7A:
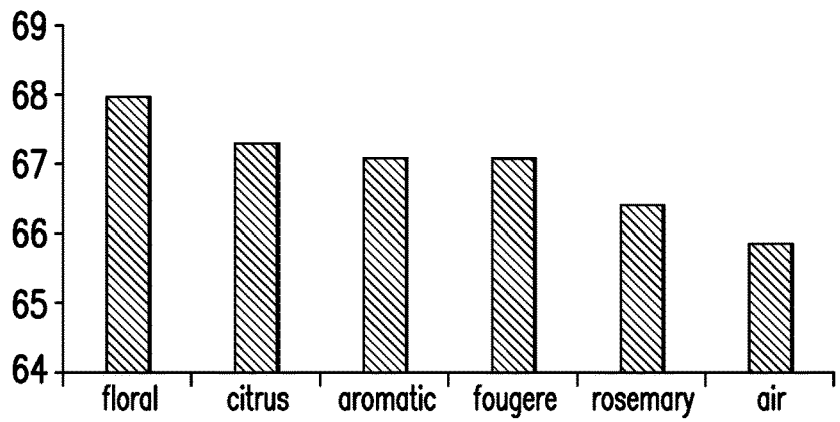
FIGS. 7A-7C show the scoring for different attributes as perceived based on kitchen images in the presence of the odorants in Example 5.
Figure 7B:
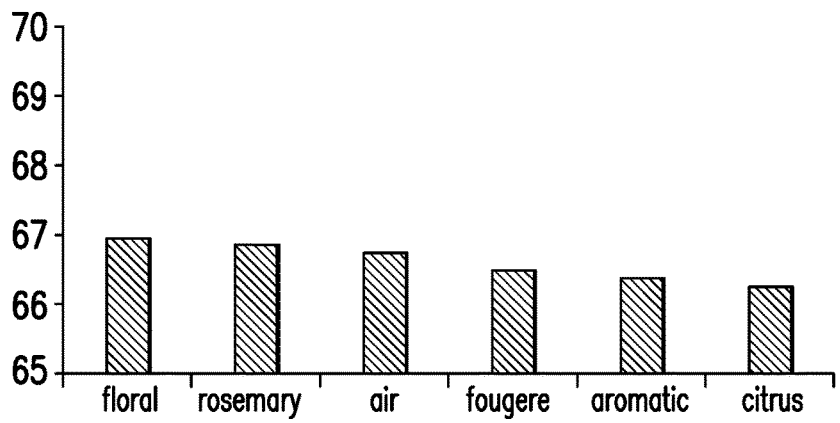
Figure 7C:
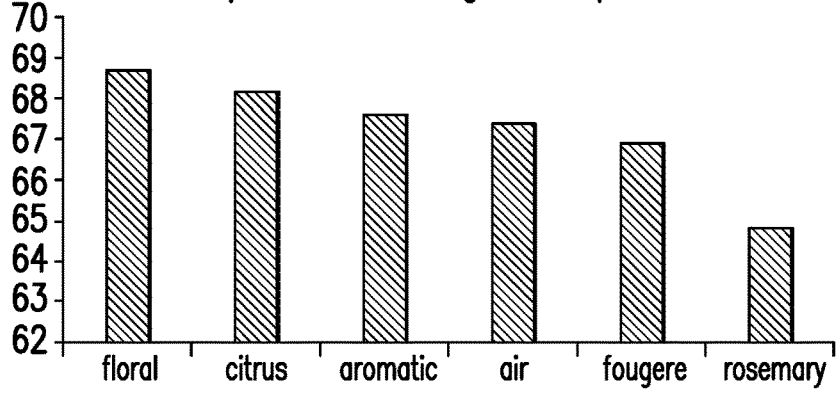

Results of the assessments are shown in FIGS. 7A-7C. The data show that there is a difference in the hygienic judgment between the olfactive directions. The floral direction enhanced the perception of the hygiene of all rooms compared to rosemary and air. The citrus direction enhanced the perception of the hygiene of all rooms compared to air. Differences were obtained regarding the complex proud/pleasing dimension. The floral direction enhanced the perception of the proud dimension of all rooms compared to rosemary and fougere. The other directions and air enhanced the perception of the hygiene of all rooms compared to rosemary.

Example 6: Impact of Odors on Varying Attributes

Example 6 is a repeated study of Example 5, with minor revisions to duration of experiments with further balancing of strength and intensity perception across odorants. Participants were shown photographs of home kitchens and home bathrooms (including bathroom surfaces and toilets). The same odorants from Example 5 were used.

Figure 8A:
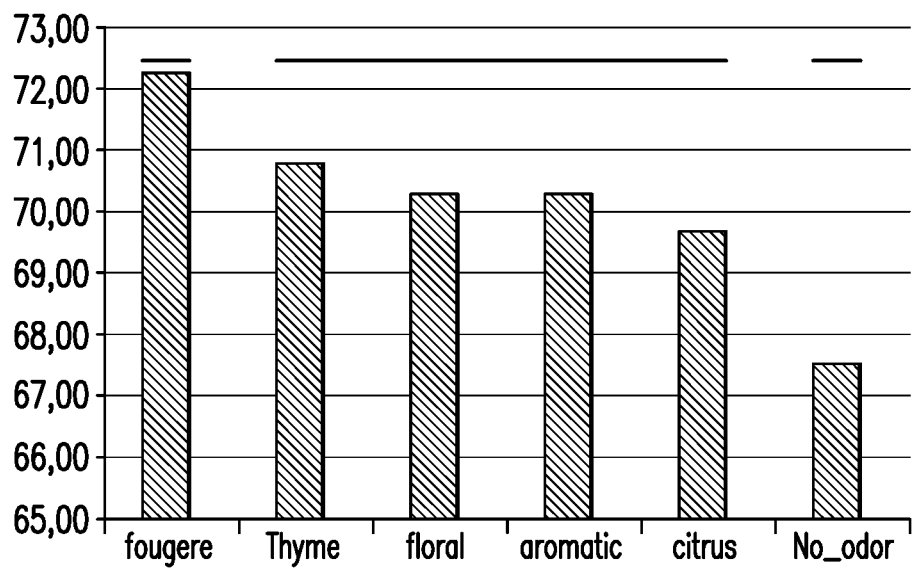
FIG. 8A-8C show the scoring for different attributes as perceived based on kitchen images in the presence of the odorants in Example 6.
Figure 8B:
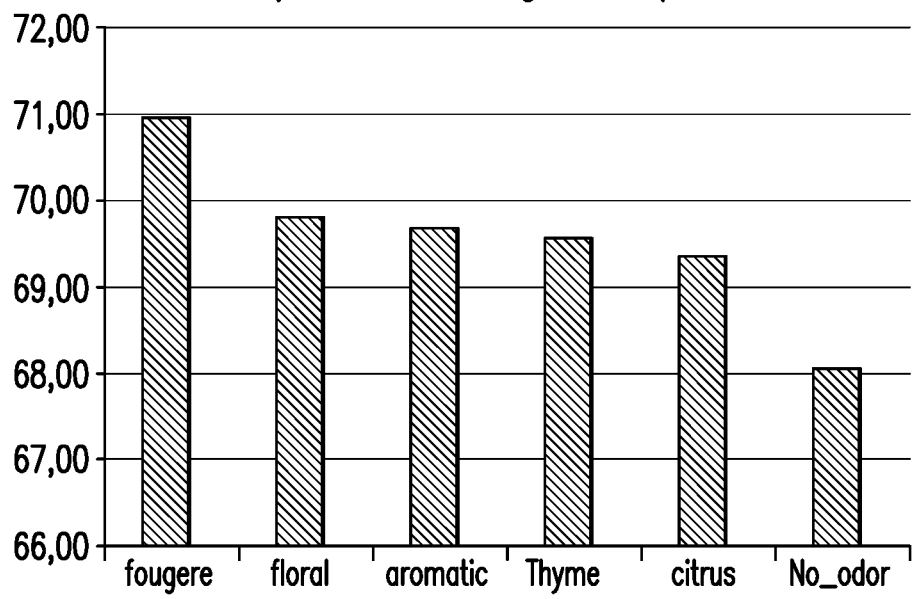
Figure 8C:
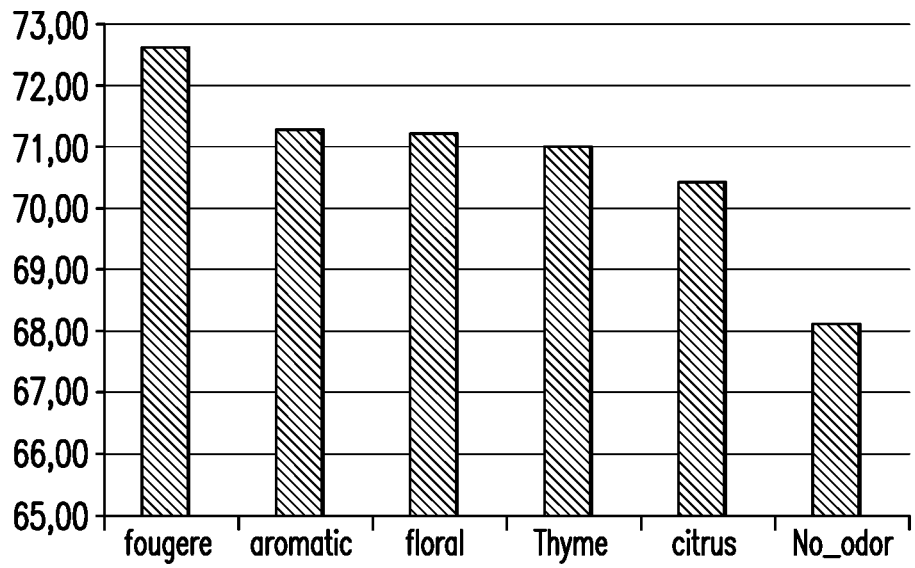
Figure 8D:
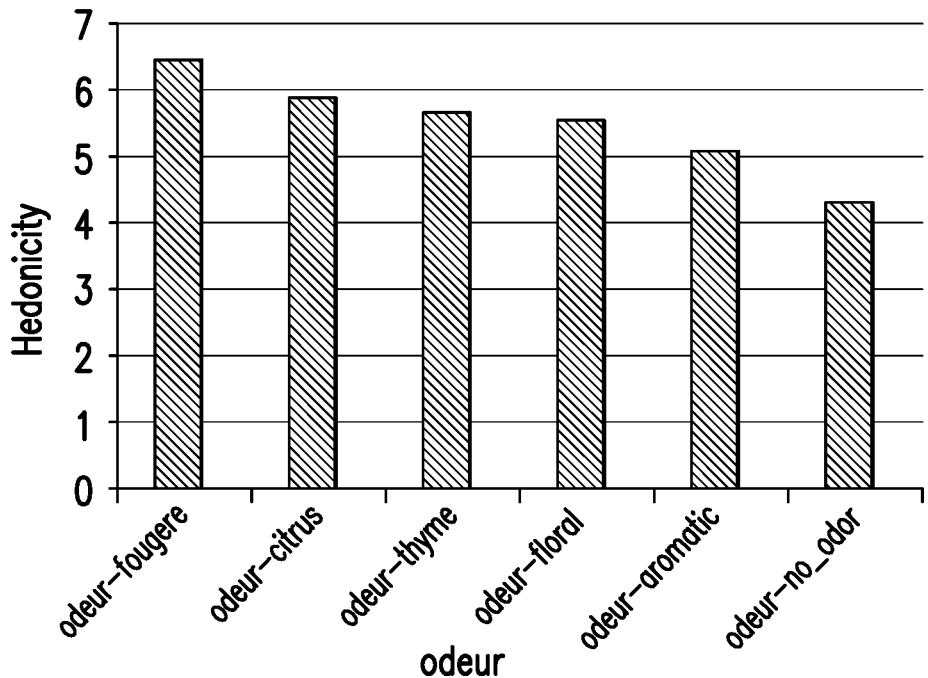
FIGS. 8D-8F show the scoring for direct assessments of the odorants in Example 6.
Figure 8E:
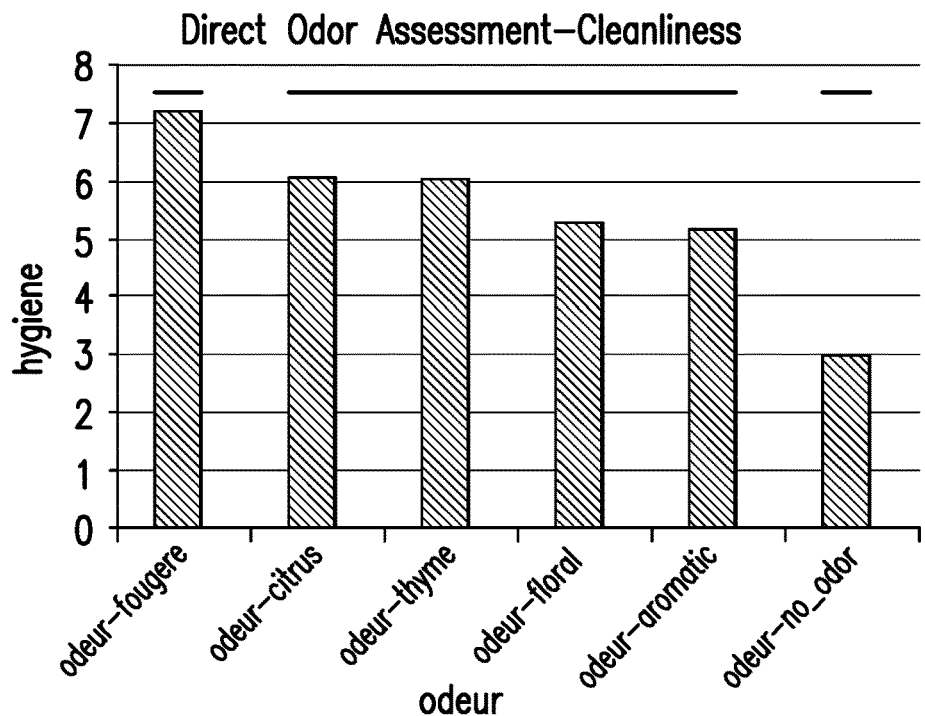
Figure 8F:
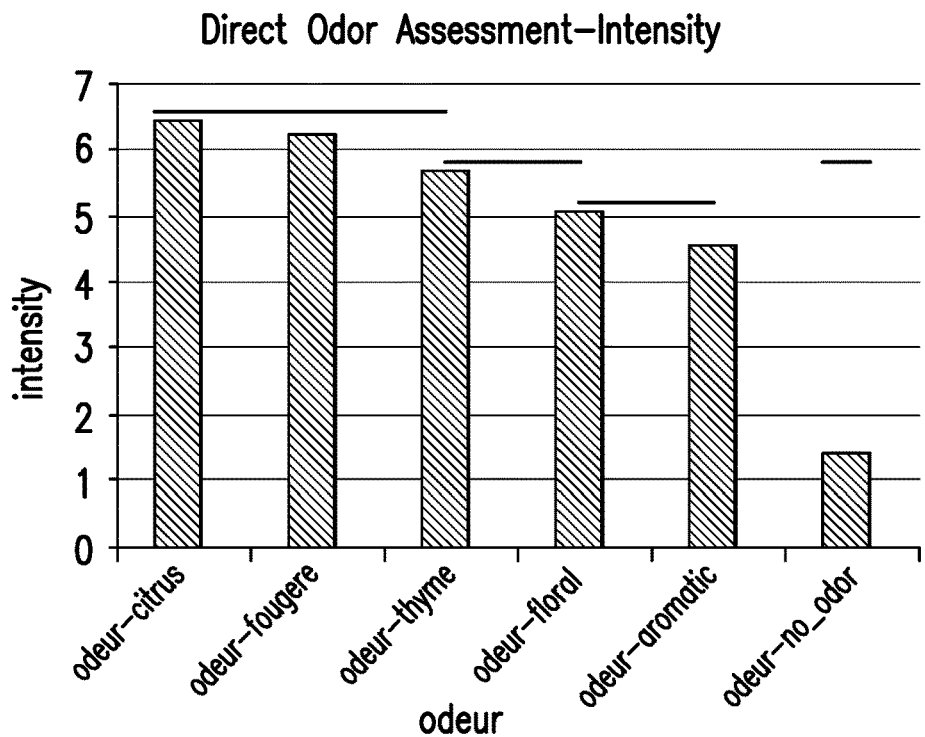

Results are shown in FIGS. 8A-8F. In FIG. 8A, the data show a very strong effect of the odorant on the hygienic variable. A key difference was that the fougere odor had the largest impact on hygiene perception. The other odorants improve the hygiene dimension compared to no odor. In FIG. 8B, the data showed a good effect on the odorants on the cleanliness dimension. In FIG. 8C, the data showed a similar strong effect of the odorant on the proud variable. The fougere odor improved the hygiene perception compared to thyme, citrus, and the blank air samples. The other odorants improved the hygiene dimension compared to the blank air. FIGS. 8D-8F show the direct assessments for the odors at the conclusion of the experiment for hedonicity, hygiene and intensity.

Example 7: Testing of Odorants with Photographs

Figure 9A:
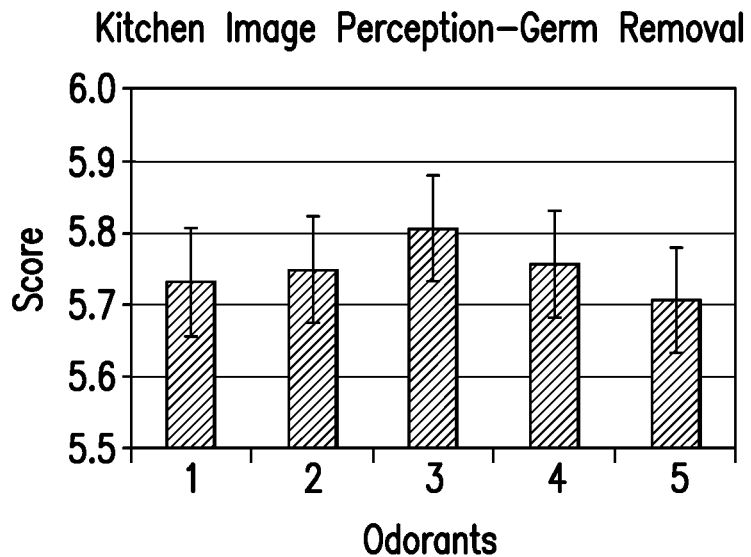
FIGS. 9A-9C show the scoring for different attributes as perceived based on kitchen images in the presence of the odorants in Example 7.
Figure 9B:
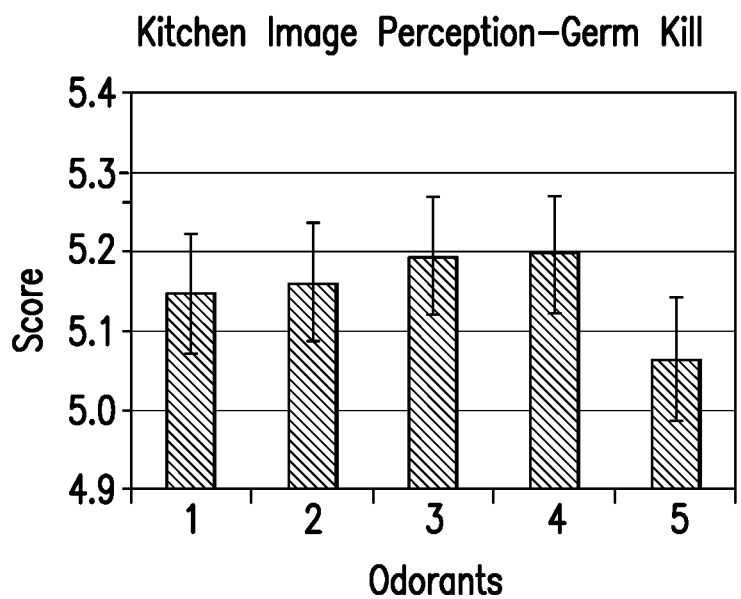
Figure 9C:
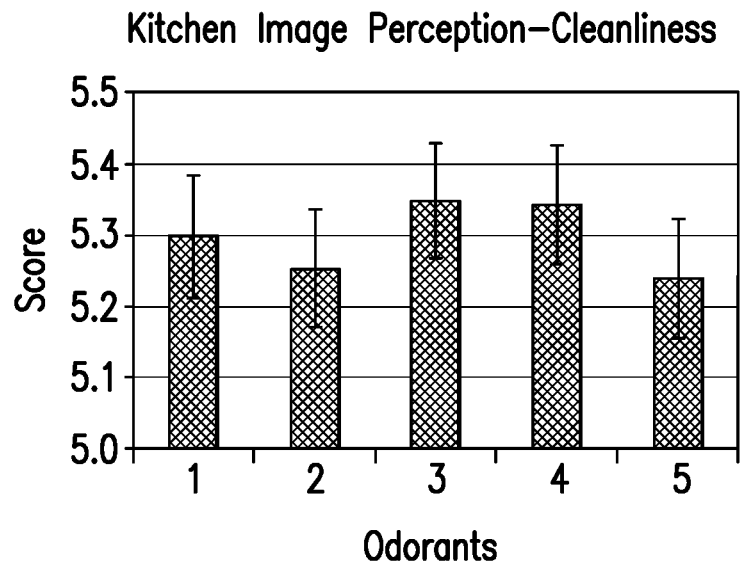
Figure 9D:
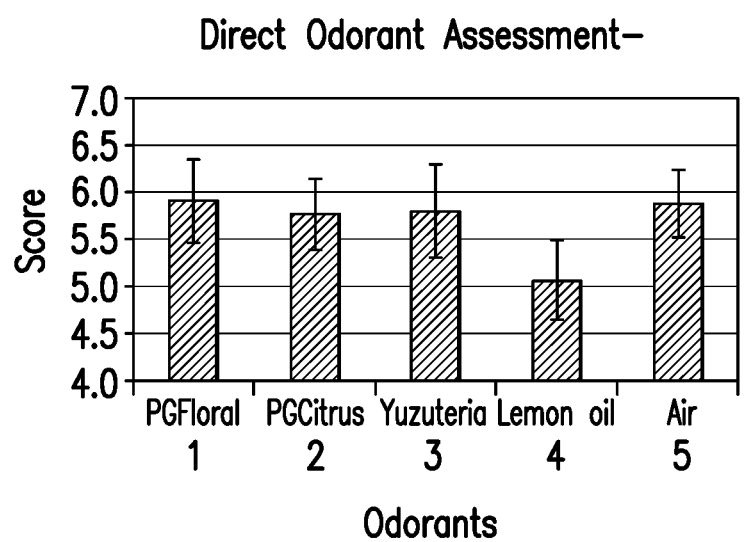
FIGS. 9D-9F show the scoring for direct assessments of the odorants in Example 7.
Figure 9E:
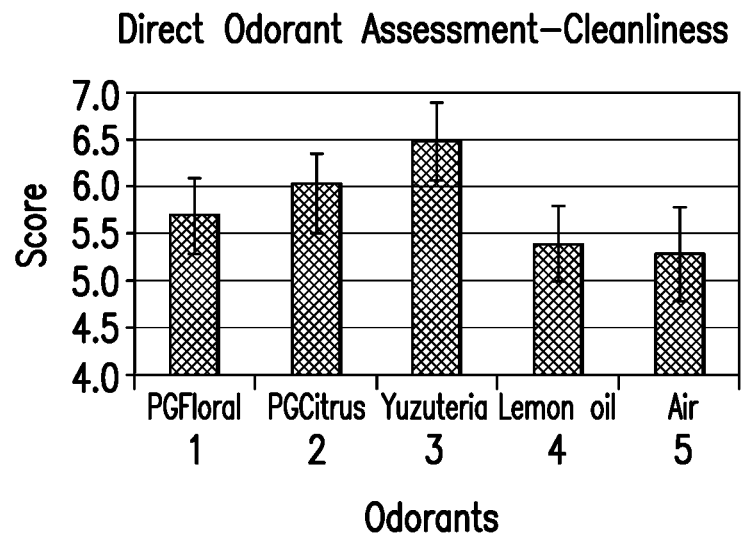
Figure 9F:
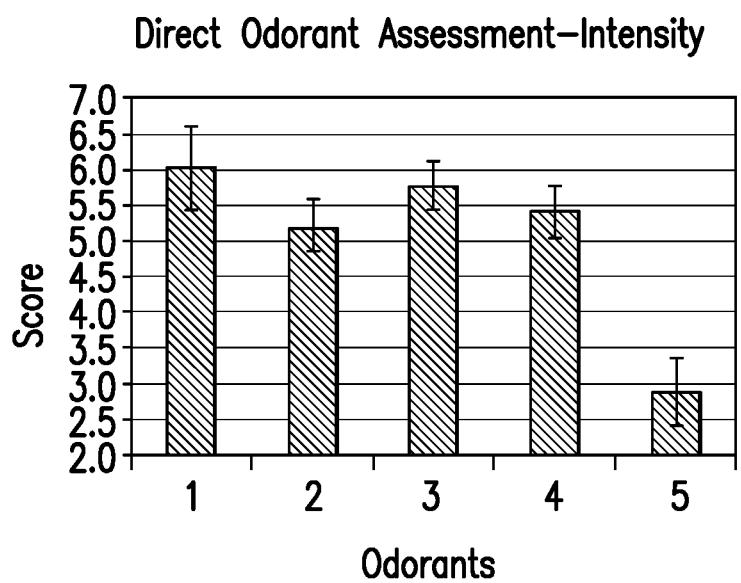

Example 7 is a Cross-Modal study that follows the testing parameters of Example 4. Each participant was shown various photographs of home kitchens. Results are shown in FIGS. 9A-9F. In FIG. 9A, the data show the results for perceived germ removal. In FIG. 9B, the data showed overall lower scores for perceived germ kill. Odorants 3 and 4 show higher scores for perceived germ kill. In FIG. 9C, the data showed that Odorants 3 and 4 were directionally higher for perceived cleanliness. FIGS. 9D-9F show the direct assessments for the odorants based on hedonicity, hygiene and intensity.

Example 8: Testing of Odorants with Photographs

Figure 10:
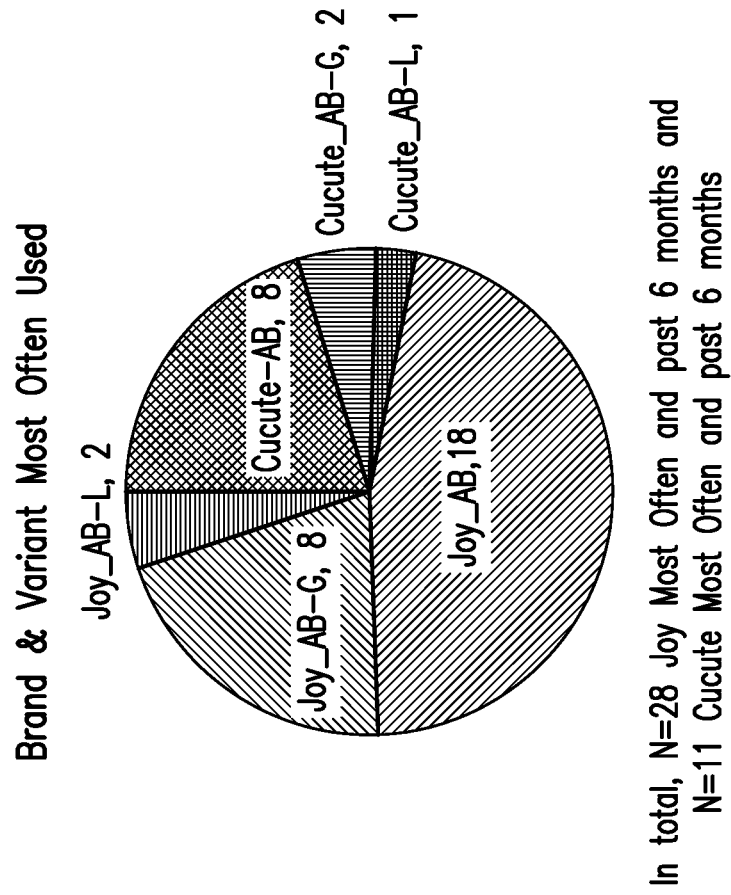
FIG. 10 shows the participant cleansing brand use history over the prior 6 months for the participants as described by Example 8.

Example 8 provides the results from a Cross-Modal study that tested the compositions of the presently disclosed subject matter. 39 female participants ranging in ages 25 to 54 were included in this study. The participants were also the primary dish washer in their homes. Each participant was shown various photographs of home kitchens, and each participant was rapidly exposed to a series of odors (separated by air). Upon exposure to a specific image-odor combination, the participants scored the photographs on a 9-point scale for different hygiene-related attributes. Participant cleansing brand use history over the past 6 months is shown in FIG. 10.

There were three test odors (#1-#3). Odor 1 was a hygiene composition with a citrus green fragrance. Odor 2 was a lemon oil control fragrance. Odor 3 was simply air (control blank).

Figure 11:
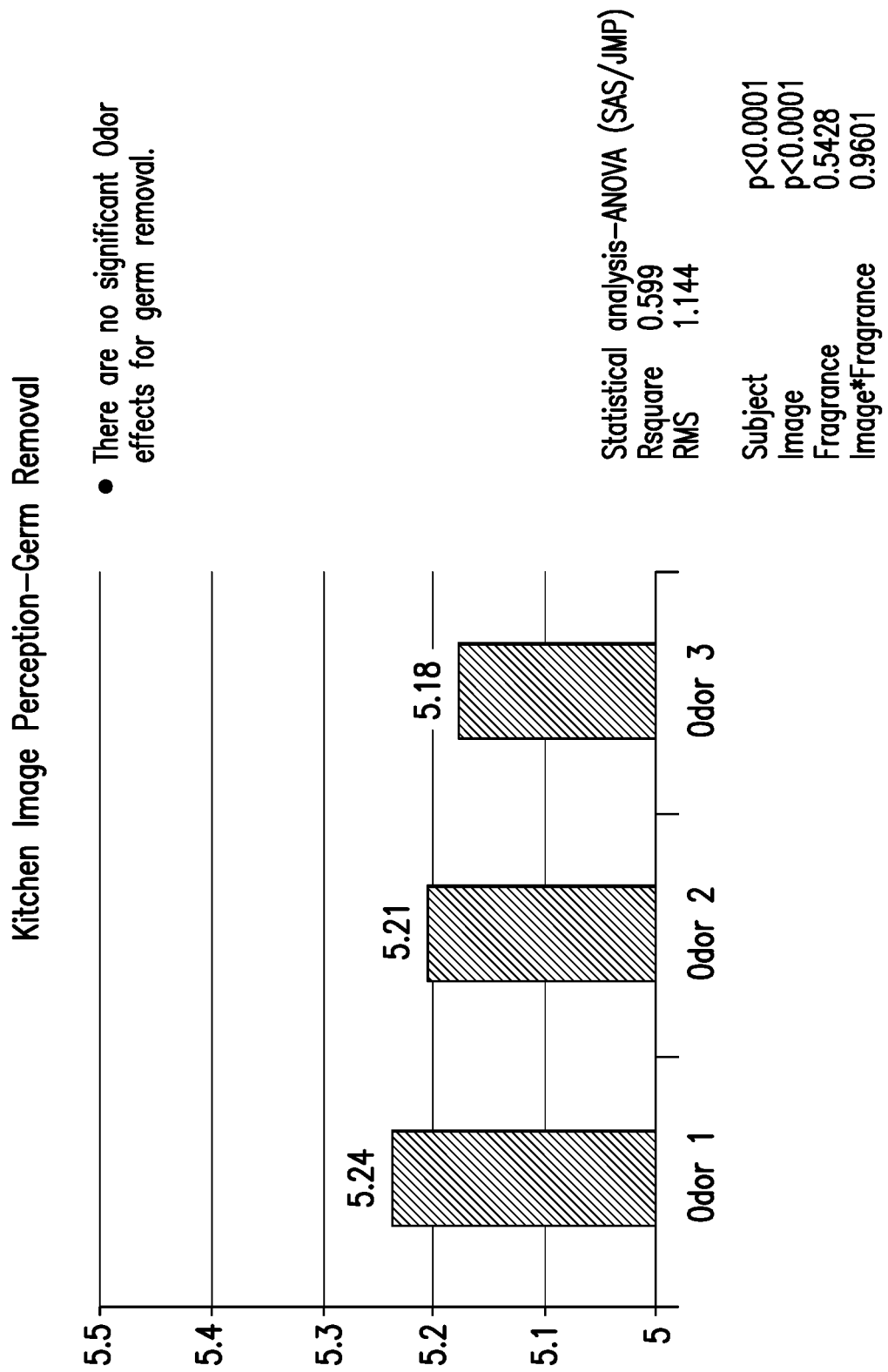
FIG. 11 shows the average assessment score for the perceived "germ removal" attribute as perceived based on kitchen images in the presence for each of odors 1-3 as described by Example 8.
Figure 12:
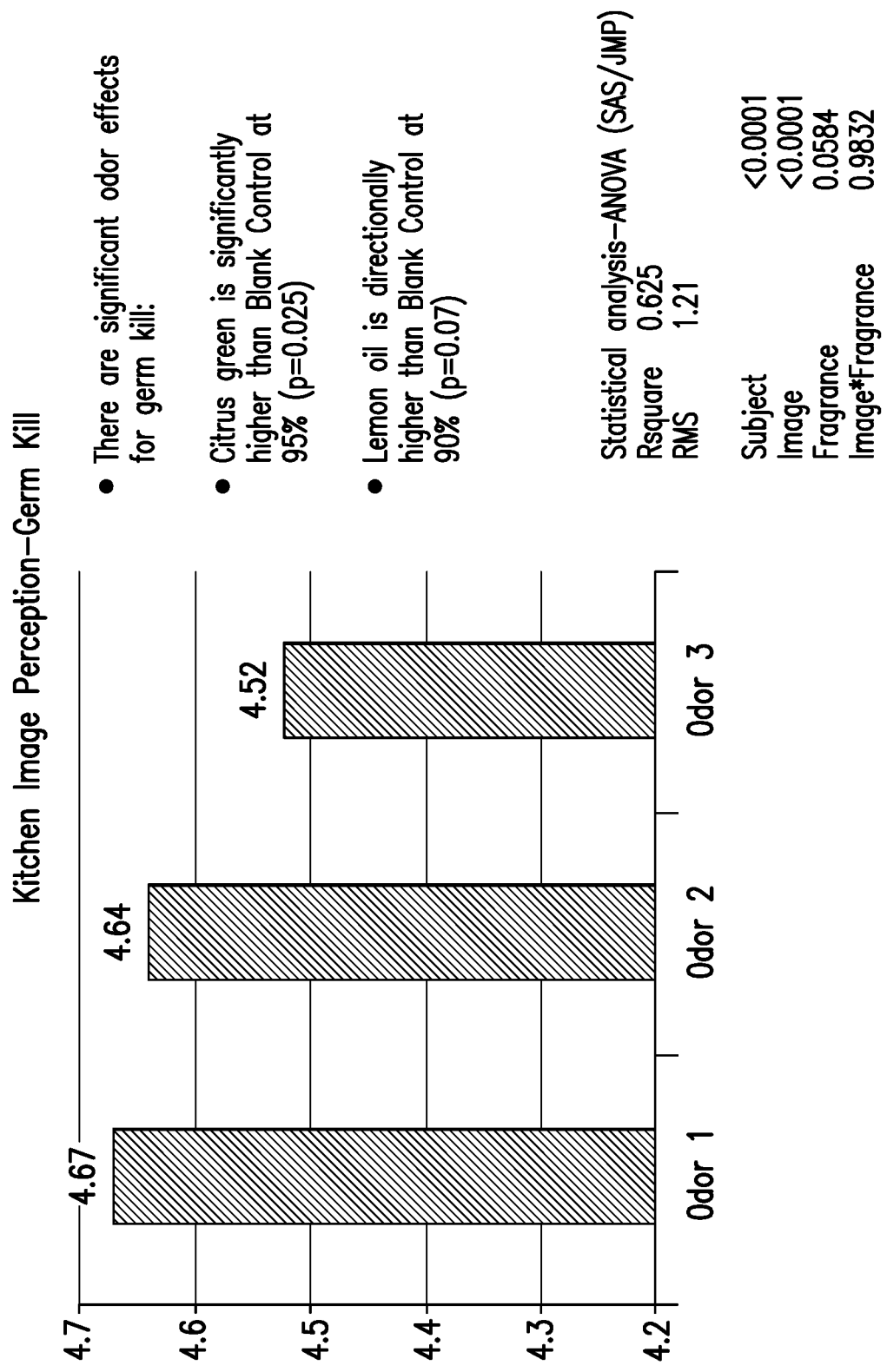
FIG. 12 shows the average assessment score for the perceived "germ kill" attribute as perceived based on kitchen images in the presence for each of odors 1-3 as described by Example 8.
Figure 13:
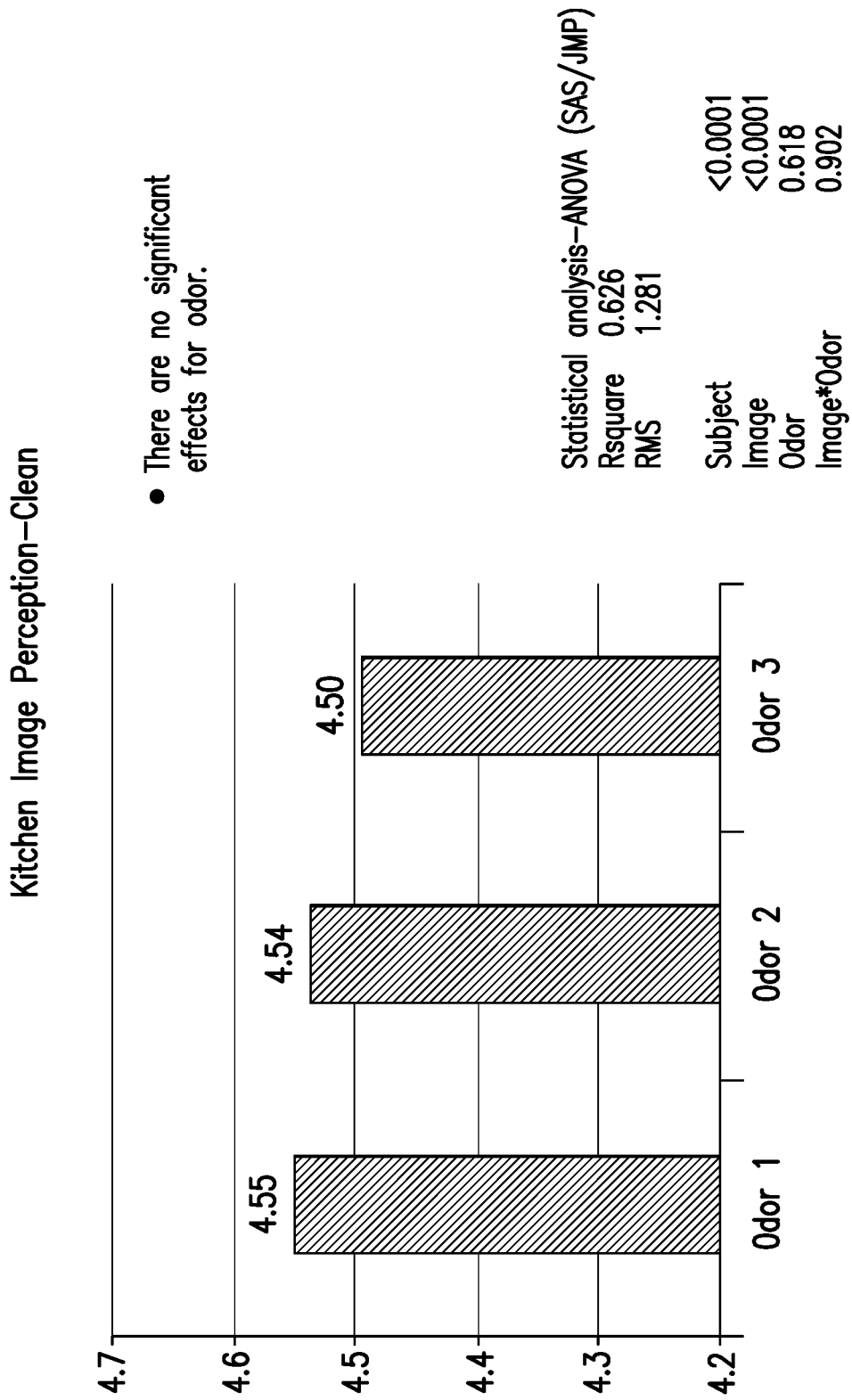
FIG. 13 shows the average assessment score for the perceived "clean" attribute as perceived based on kitchen images in the presence for each of odors 1-3 as described by Example 8.
Figure 14:
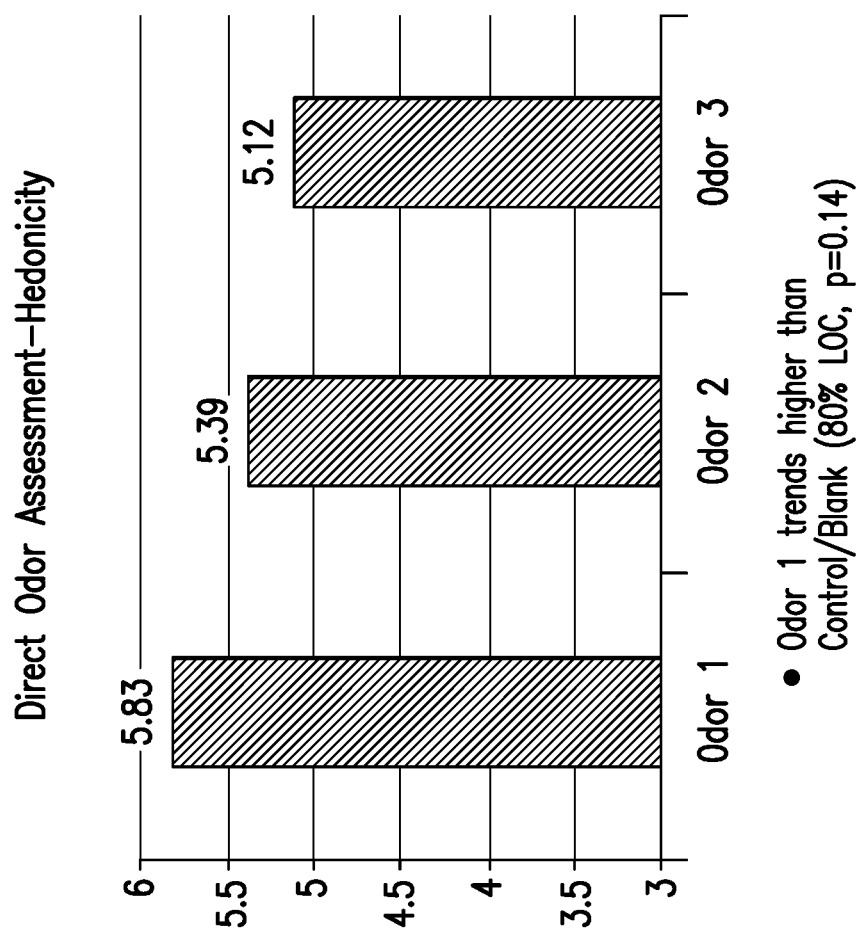
FIG. 14 shows the average direct odor assessment score for the impression of "hedonicity" for each of odors 1-3 as described by Example 8.
Figure 15:
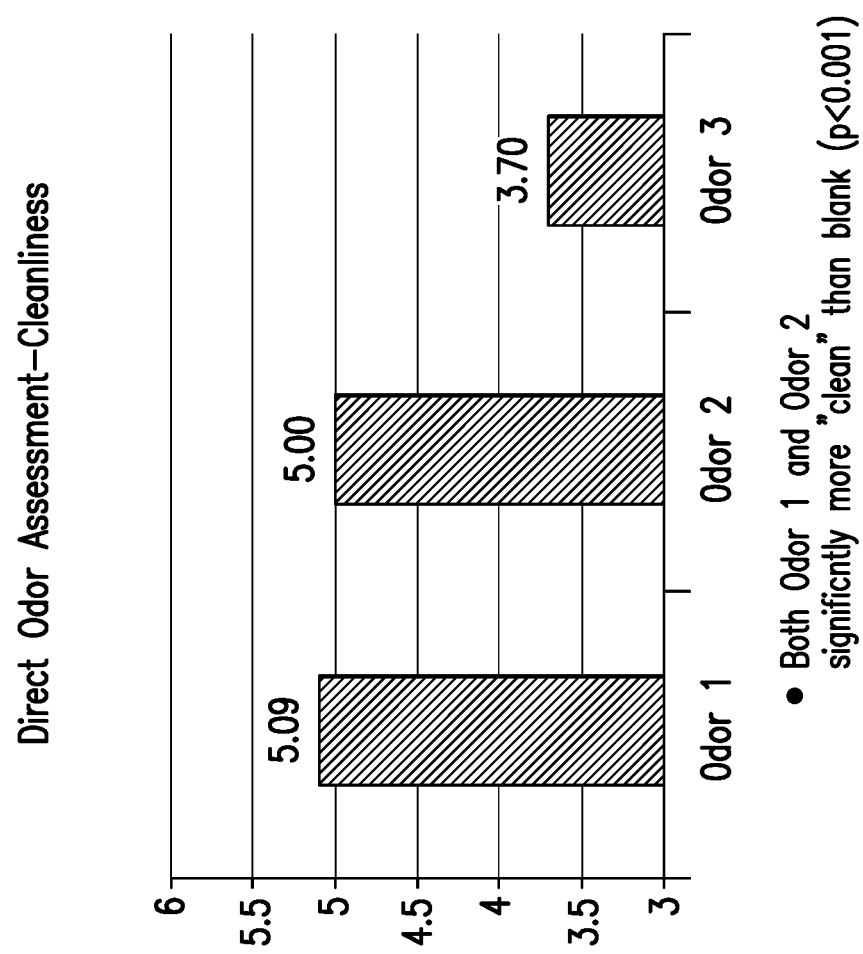
FIG. 15 shows the average direct odor assessment score for the impression of "cleanliness" for each of odors 1-3 as described by Example 8.
Figure 16:
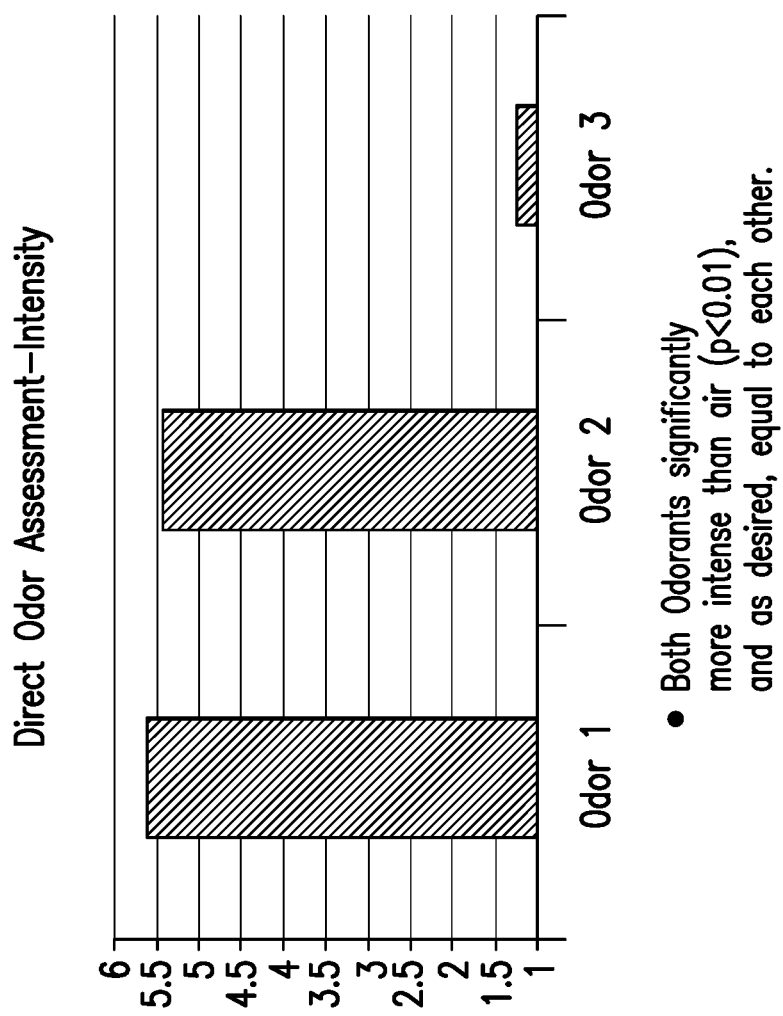
FIG. 16 shows the average direct odor assessment score for the impression of "intensity" for each of odors 1-3 as described by Example 8.
Figure 17:
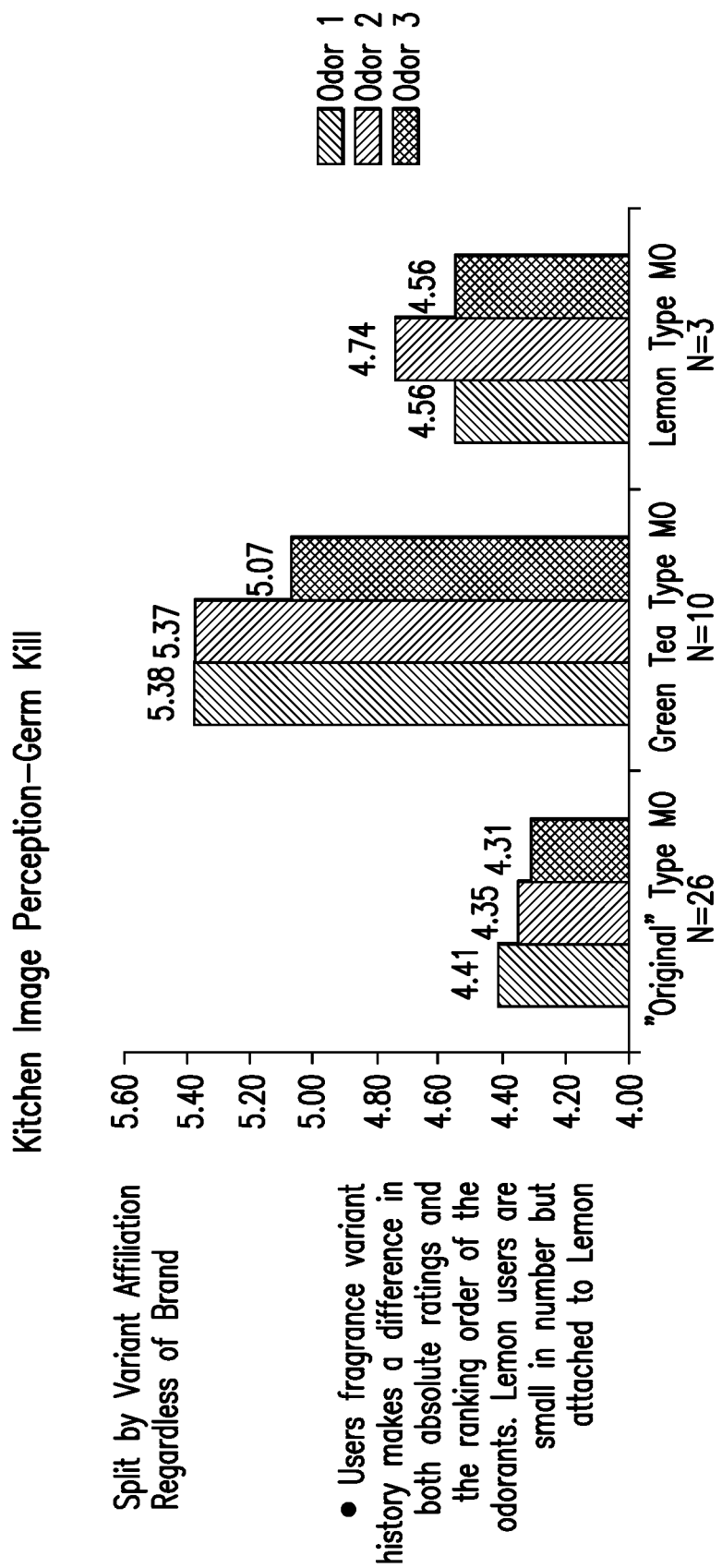
FIG. 17 shows the average assessment score for the "germ kill" attribute as perceived based on kitchen images in the presence of odors 1-3 as described by Example 8, further split by participant's stated history of using various commercially available dish cleaning scent types.
Figure 18:
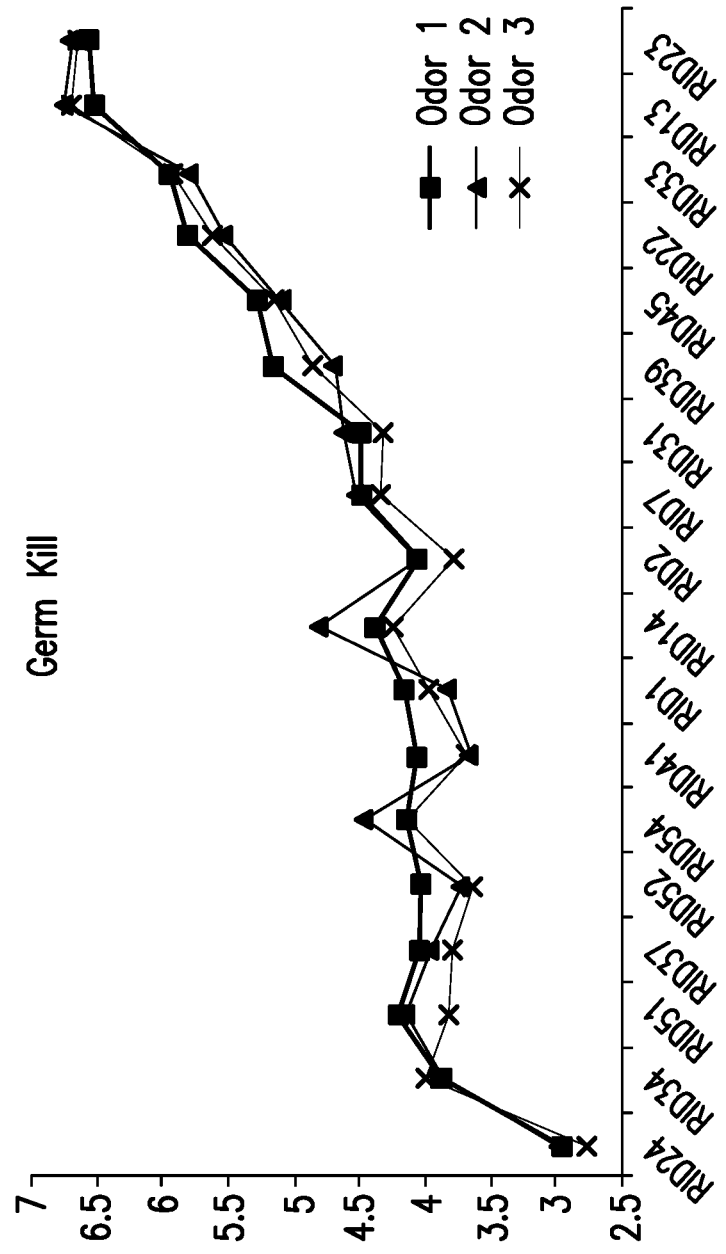
FIG. 18 shows the average assessment score for the perceived "germ kill" attribute for each of the kitchen images tested with each of odors 1-3 as described by Example 8.
Figure 19:
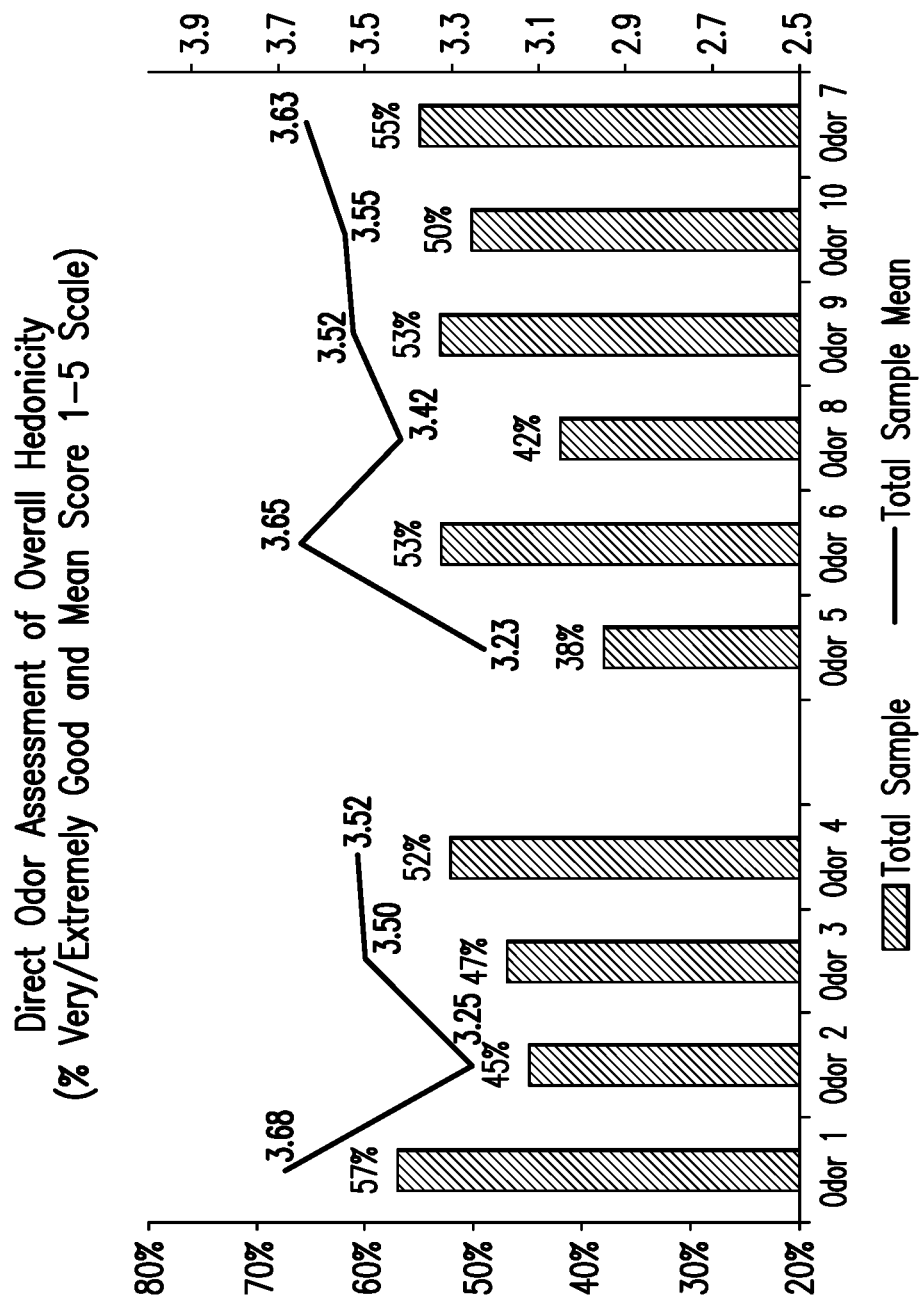
FIG. 19 shows the participants' overall rating of the odors based on direct smelling as described by Example 9.
Figure 20:
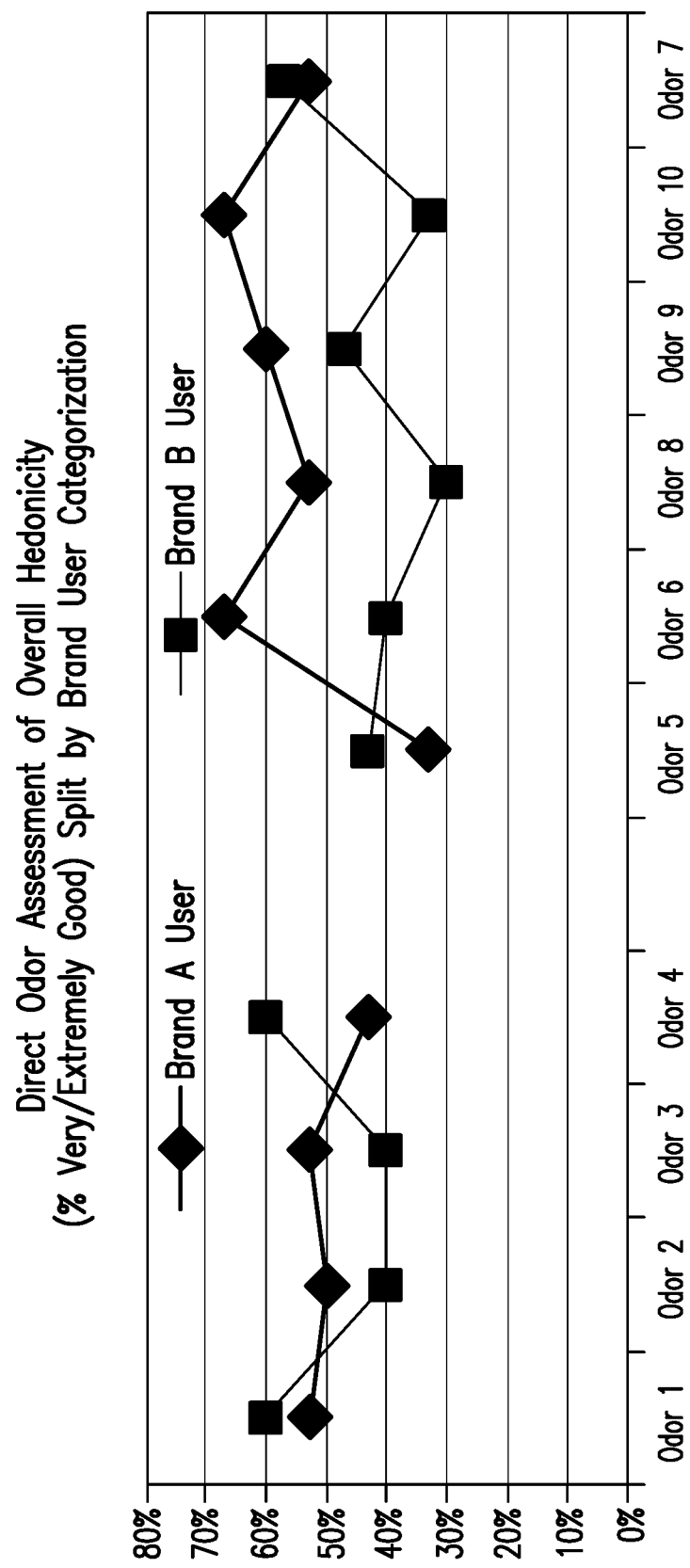
FIG. 20 shows the participants' overall rating of the odors categorized by participant's historical use of various dish cleaner brands as described by Example 9.
Figure 21:
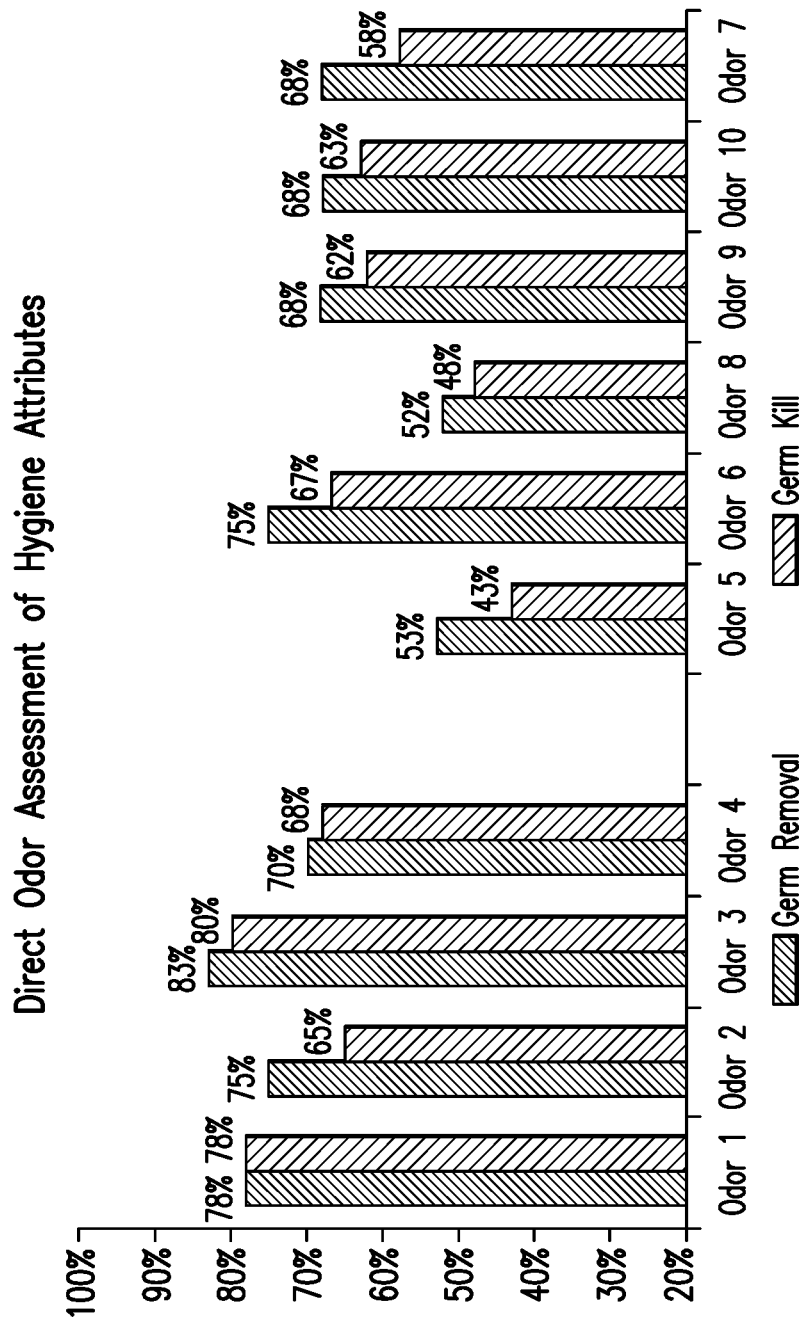
FIG. 21 shows the participants' perception of the hygiene related attributes "germ kill" and "germ removal" by directed smelling of the odorants described by Example 9.
Figure 22:
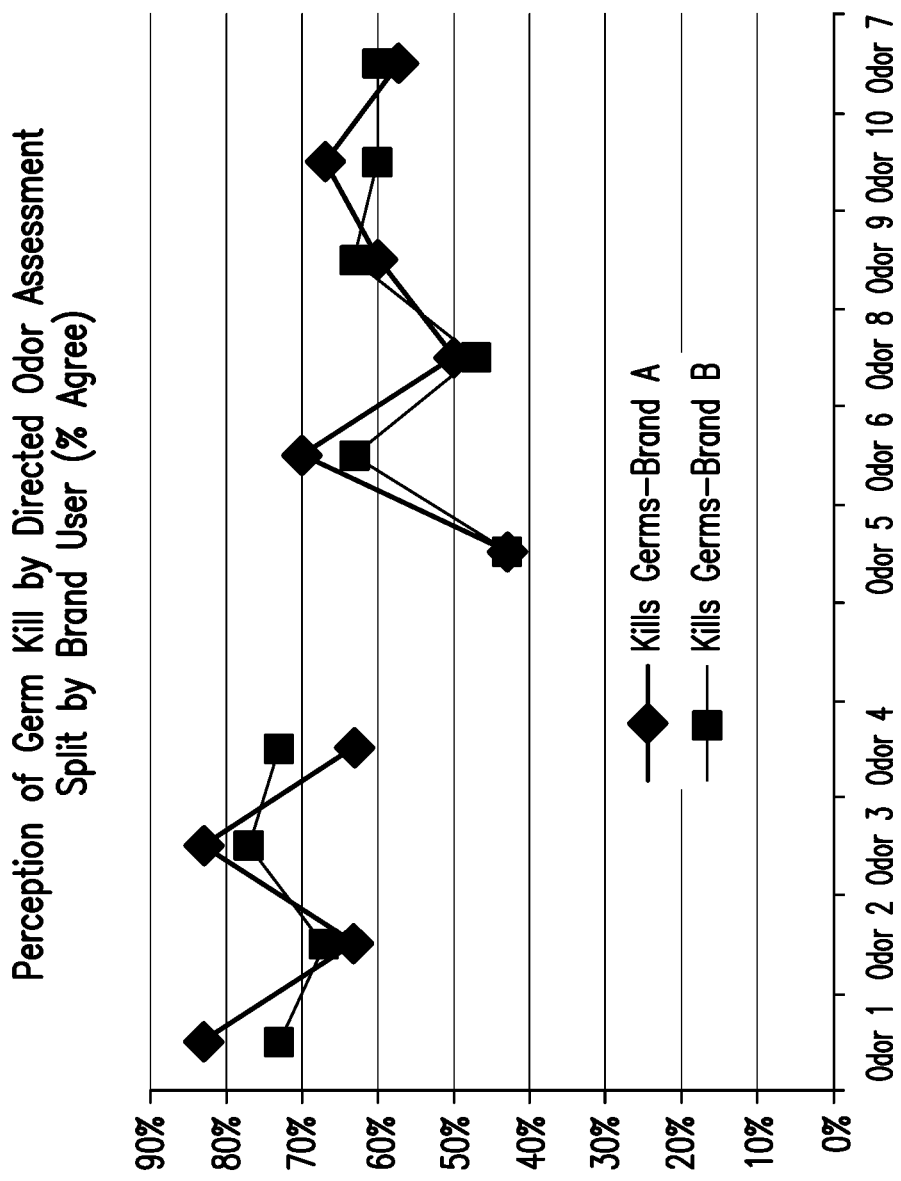
FIG. 22 shows the participants' perception of the hygiene attribute "germ kill" based on direct smelling of the odors described by Example 9 categorized by the type of fragrance cleaner brand historically used by the participant.
Figure 23:
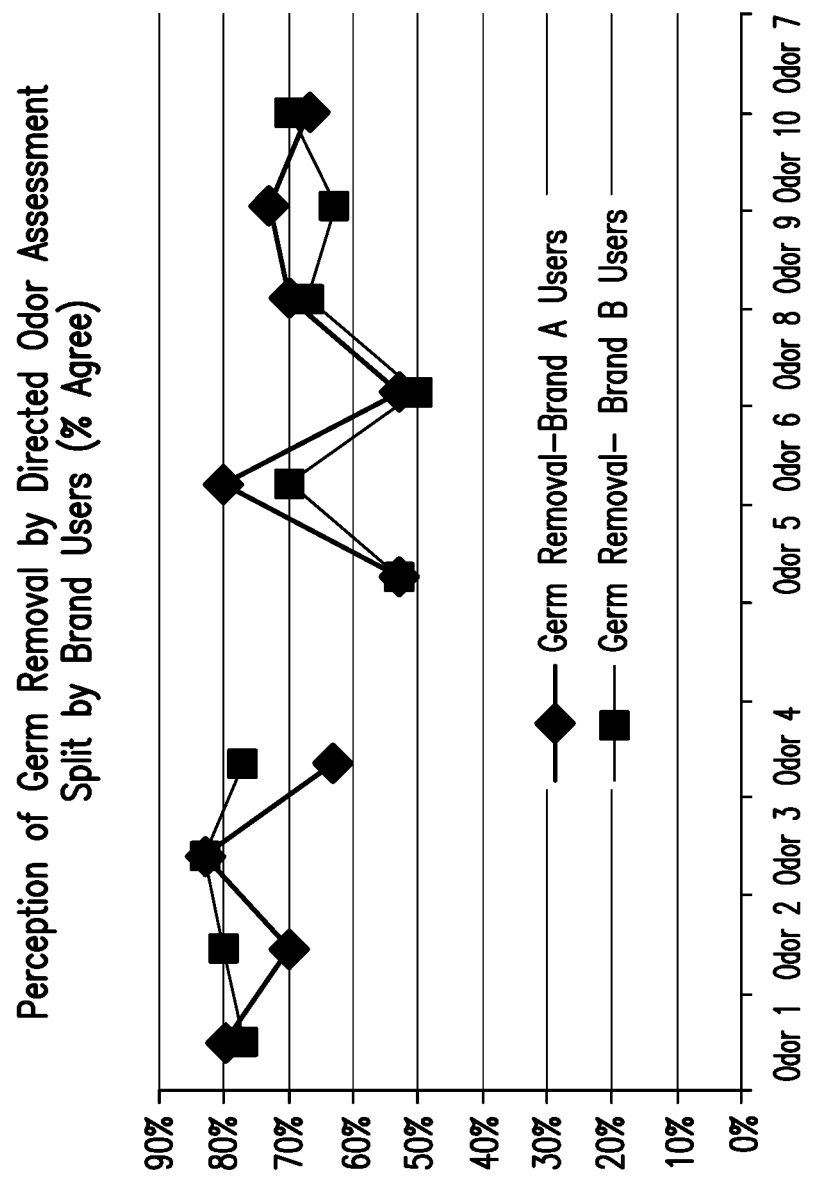
FIG. 23 shows the participants' perception of the hygiene attribute "germ removal" based on direct smelling of the odors described by Example 9 categorized by the type of fragrance cleaner brand historically used by the participant.
Figure 24:
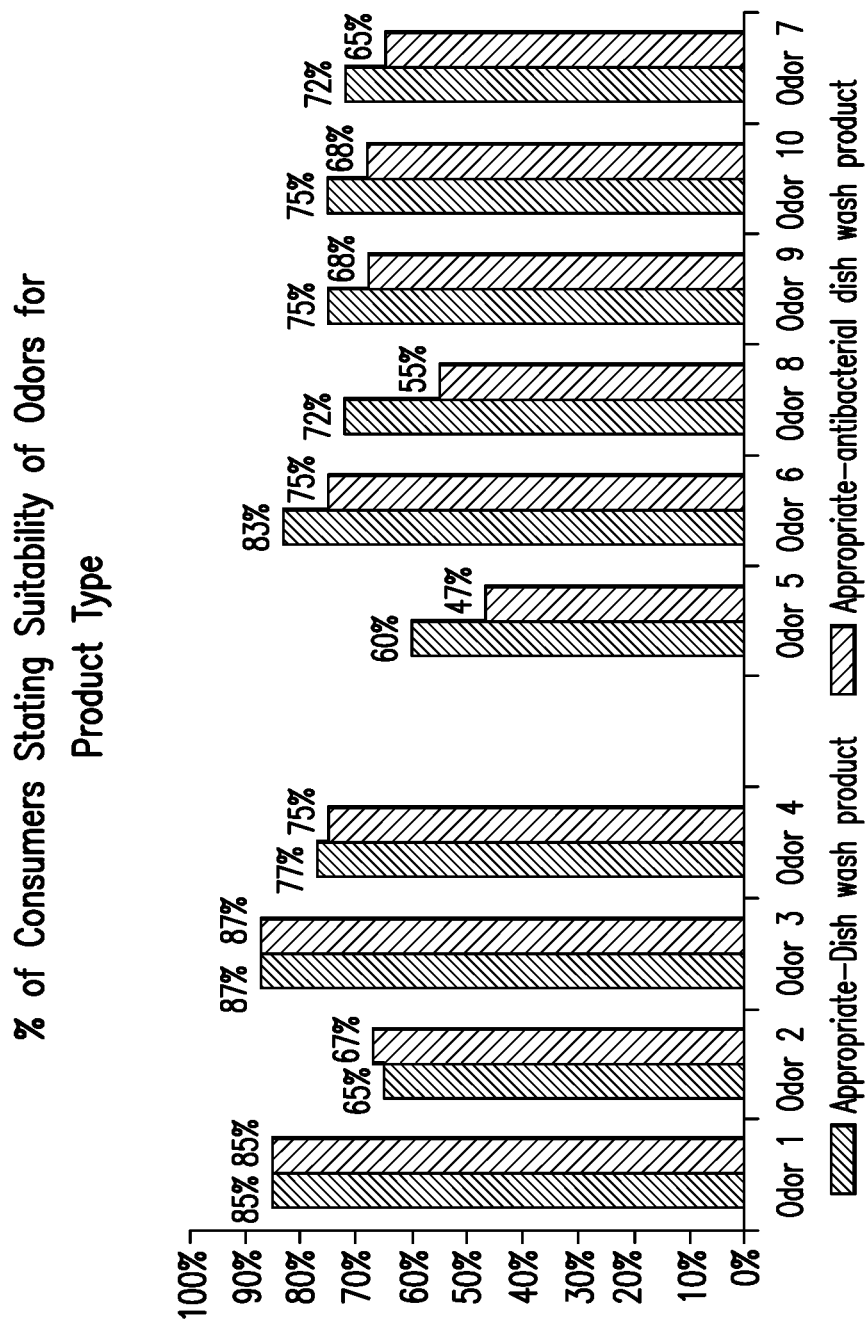
FIG. 24 shows the participants' perception of product suitability for the odors described by Example 9.
Figure 25:
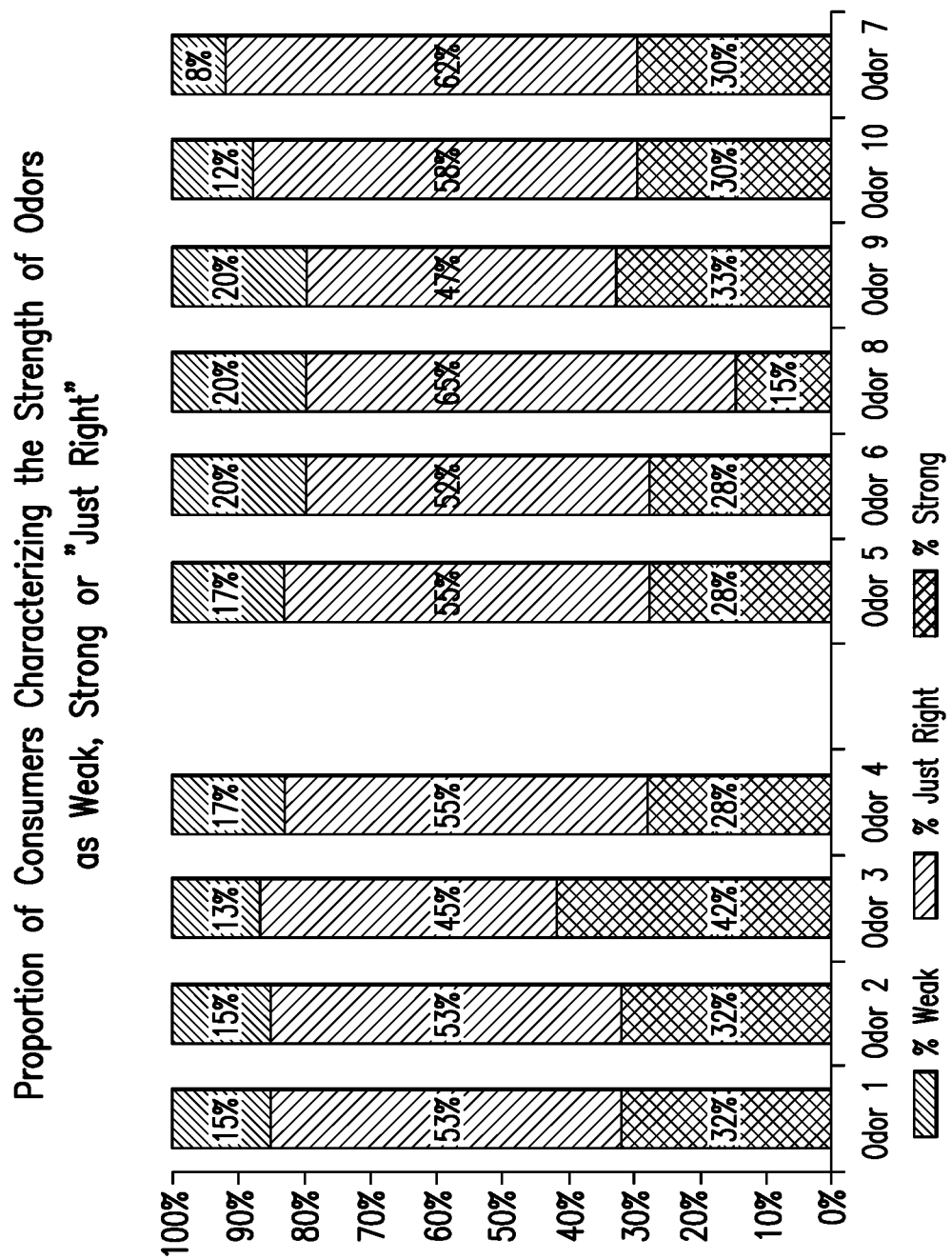
FIG. 25 shows the participants' perception of product intensity/strength for the odors described by Example 9.

There were three perceived attributes that were assessed: germ removal, germ kill and clean. Results of the scoring are shown in FIGS. 11-13. At the conclusion of the Cross-Modal experiment, participants were then asked to smell the odors again and self-report their impressions of hedonicity, intensity, and cleanliness of each odor on the same scale. Results of the self-reporting are shown in FIGS. 14-16. Assessment of perceived germ kill by participant cleansing brand use history and cleansing fragrance use history is shown in FIG. 18. Assessment of perceived germ kill for each of the kitchen images is shown in FIG. 18.

The results showed that Odor 1 and Odor 2 had similar scores that were higher than air across all attributes. Perceived germ kill assessments were lower than perceived germ removal. Previous brand usage history impacts results of attribute assessment.

Example 9: Consumer Testing

Example 9 is a Central Location Test (CLT) study of the odors which provides results regarding the compositions of the presently disclosed subject matter. In particular, the study was to identify the portion(s) of the fragrance most responsible for cuing efficacy and hygiene.

60 female participants ranging in ages 18 to 55 were included in this study. The participants were also the primary dish washer in their homes. Each participant stated that "antibacterial" is an important quality in the choice of their dish washing product. Half of the users use Brand Product A most often over the past six months, and the other half used Brand Product B the most over the past six months. Each participant was presented four odor accords (randomized) and six finished products with different amounts of the odor accords (randomized). Upon exposure and directed smelling of each specific odor, the participants self-reported a series of scores for each odor as to whether or not it embodied a particular attribute or fragrance. Participants also scored the scents on a 9-point scale for certain attributes.

There were ten odors (#1-#10). Odor 1 was Accord A (citrus green fragrance). Odor 2 was Accord B (floral fragrance). Odor 3 was Accord C (herbal green rebalance fragrance). Odor 4 was Accord D (floral aldehyde rebalance fragrance). Odor 5 was a floral fragrance with control odor. Odor 6 was a floral fragrance with Accord A at a ratio of 6:4. Odor 7 was a floral fragrance with Accord A at a higher level. Odor 8 was a floral fragrance with Accord B at a ratio of 8:2. Odor 9 was a floral fragrance with Accord C at a ratio of 7:3. Odor 10 was a floral fragrance with Accord D at a ratio of 6:4.

There were five perceived attributes that were assessed: overall hygiene, germ removal, germ kill, suitability for a hand dish soap and perceived strength. Results of the scoring are shown in FIGS. 19-25. Participants were then asked to report whether the odor contained a particular fragrance. Results of perceived fragrance are shown in Table 11 (numbers in percentages). Participants were also asked to report whether the odor embodied a particular functional attribute. Results of perceived functional attribute are shown in Table 12 (numbers in percentages).

TABLE 11

|  | 1 | 2 | 3 | 4 | 5 | 6 | 7 | 8 | 9 | 10 |
|---|---|---|---|---|---|---|---|---|---|---|
| Citrus | 83 | 63 | 82 | 82 | 22 | 65 | 37 | 48 | 57 | 63 |
| Fruity | 62 | 30 | 42 | 55 | 40 | 57 | 50 | 47 | 48 | 50 |
| Herbal/ Leafy | 23 | 50 | 30 | 23 | 13 | 18 | 12 | 22 | 10 | 15 |
| Airy breezy | 18 | 20 | 17 | 12 | 17 | 15 | 25 | 15 | 10 | 13 |
| Artificial | 15 | 25 | 20 | 20 | 32 | 12 | 7 | 12 | 25 | 20 |
| Sweet | 8 | 5 | 2 | 10 | 20 | 17 | 18 | 15 | 13 | 13 |
| Floral | 5 | 5 | 3 | 5 | 33 | 23 | 33 | 20 | 28 | 27 |
| Watery Marine | 5 | 10 | 10 | 10 | 20 | 15 | 13 | 15 | 12 | 13 |
| Perfume | 3 | 5 | 8 | 5 | 18 | 12 | 17 | 22 | 18 | 13 |
| Woody | 3 | 30 | 18 | 12 | 7 | 5 | 7 | 10 | 7 | 5 |
| Cosmetic | 0 | 0 | 0 | 0 | 5 | 3 | 10 | 3 | 5 | 3 |
| Soapy | 0 | 3 | 2 | 2 | 13 | 2 | 17 | 10 | 8 | 5 |

TABLE 12

|  | 1 | 2 | 3 | 4 | 5 | 6 | 7 | 8 | 9 | 10 |
|---|---|---|---|---|---|---|---|---|---|---|
| Fruity | 93 | 72 | 87 | 87 | 65 | 88 | 80 | 82 | 82 | 83 |
| Clean tough food/grease | 90 | 70 | 82 | 82 | 55 | 75 | 63 | 73 | 67 | 67 |
| Clean | 90 | 73 | 87 | 82 | 67 | 88 | 80 | 87 | 80 | 77 |
| Keeps skin soft | 63 | 62 | 60 | 60 | 70 | 70 | 77 | 67 | 72 | 62 |
| Leaves dishes shiny | 80 | 62 | 75 | 65 | 48 | 72 | 53 | 65 | 62 | 65 |

Accords A, C, and D showed high potential to be active. These Accords can improve a finished fragrance from a different olfactive family.

Attribute deltas for fragrance plus accord versus control were larger for hygiene and functionality benefits than they were for hedonics or other attributes; this suggests that the Accords were driving these benefits.

Addition of any of the Accords (particularly Accord A and C) improved functionality perception to the same extent. Accord A (Citrus Green component) and Accord C (Herbal Green Citrus component Rebalanced) showed the greatest promise for cuing hygiene benefits (although hedonics of Accord D married well with the tested floral fragrance). Accord A seemed to drive the benefit the most holistically across user groups while also carrying hedonics.

The results showed that brand usage had no significant effect on the perception of germ kill or germ removal; although, the groups do have somewhat different hedonic preferences.

Example 10: Consumer Testing with Existing Perfumes

Example 10 provides the results from a Cross-Modal study that tested the compositions of the presently disclosed subject matter in combination with existing perfumes. In this Example, a hygiene composition was used in combination with a floral fragrance, which is referred to as "Fragrance A" in this Example and the accompanying figures.

39 female participants ranging in ages 25 to 54 were included in this study. The participants were the primary dish washer in their homes and reported washing their hands at least five times per week. Each participant stated that "antibacterial" is a "very important" or "somewhat important" quality in their choice of products. 19 of the 39 participants used Fragrance A dish washing products most often. The remaining 20 participants used Fragrance B dish washing products most often. Moreover, each participant was asked to select a preferred dish washing product scent from among "Original Clean," "Green Tea," and "Lemon." Preference information for the dataset is summarized in Table 13.

TABLE 13

|  | "Original Clean" | "Green Tea" | "Lemon" |
|---|---|---|---|
| Fragrance A | n = 10 | n = 5 | n = 5 |
| Fragrance B | n = 9 | n = 5 | n = 5 |
| TOTAL | N = 19 | N = 10 | N = 10 |

The participants scored the products in a Cross-Modal test from 0 to 100. Each participant was exposed to each of Odors 1-5, while viewing 18 images per odor. Odor 1 was a negative control (air) and Odor 2 was a positive control (lemon oil). Odor 3 was a hygiene composition. Odor 4 was Fragrance A. Odor 5 was Fragrance A in combination with the hygiene composition at a ratio of 6:4. The hygiene composition had the composition of Accord A in Table 2.

Figure 26:
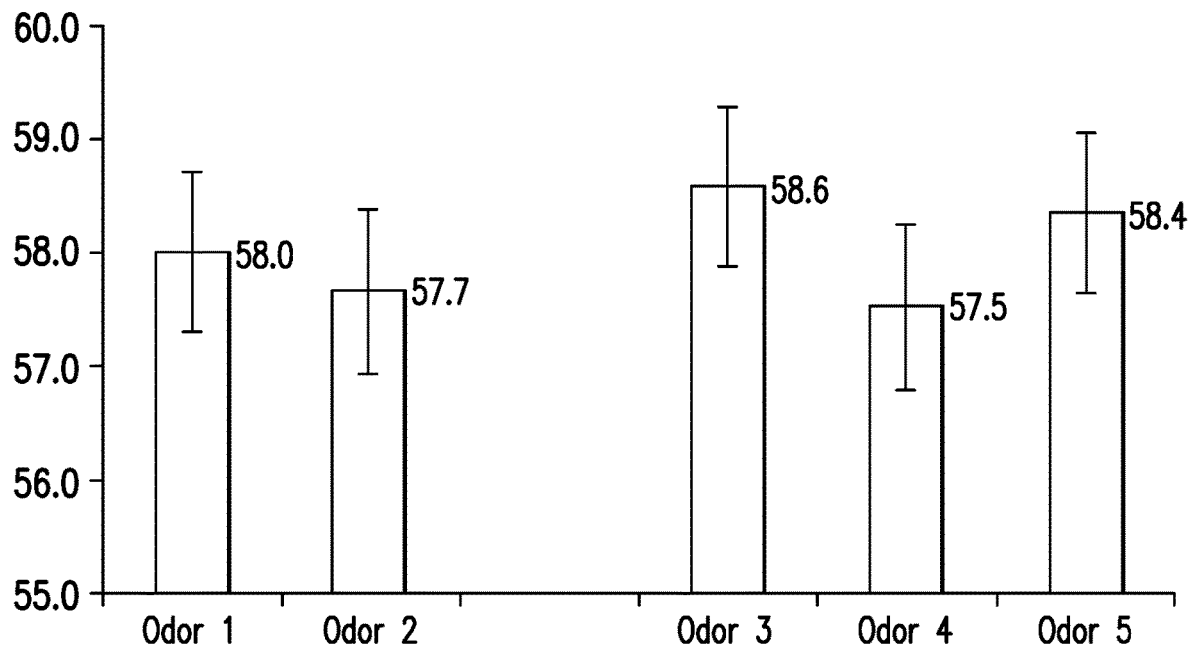
FIG. 26 shows the Non-Lemon users' perception of the attribute "germ removal" as described by Example 10.
Figure 27:
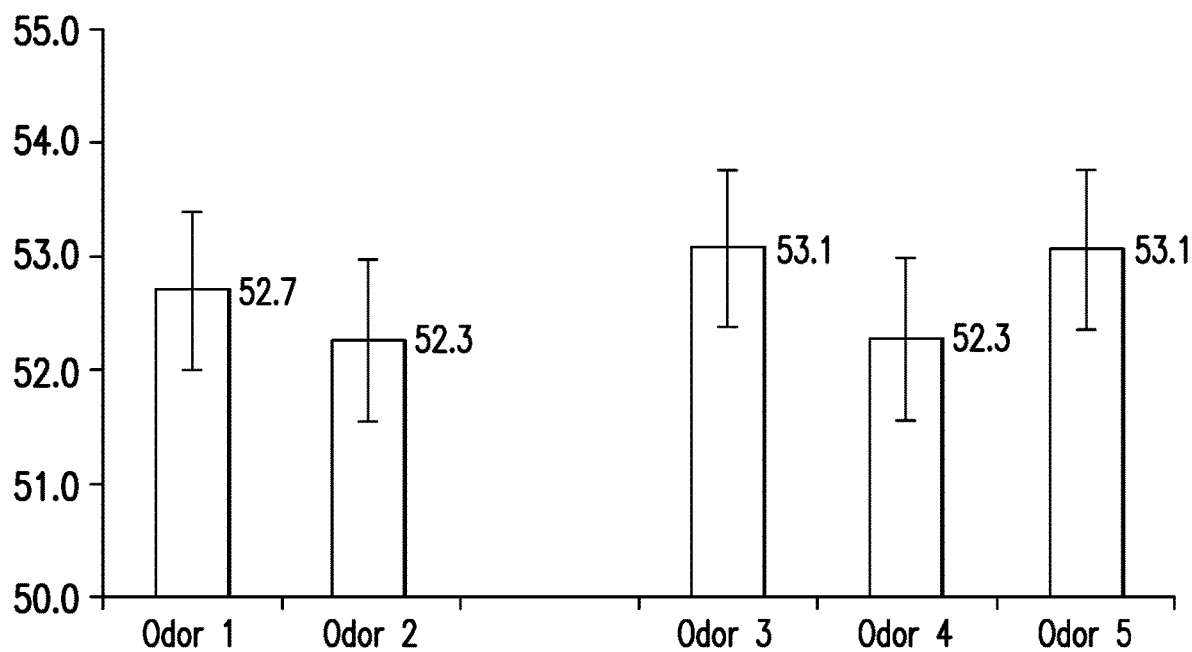
FIG. 27 shows the Non-Lemon users' perception of the hygiene attribute "germ kill" as described by Example 10.
Figure 28:
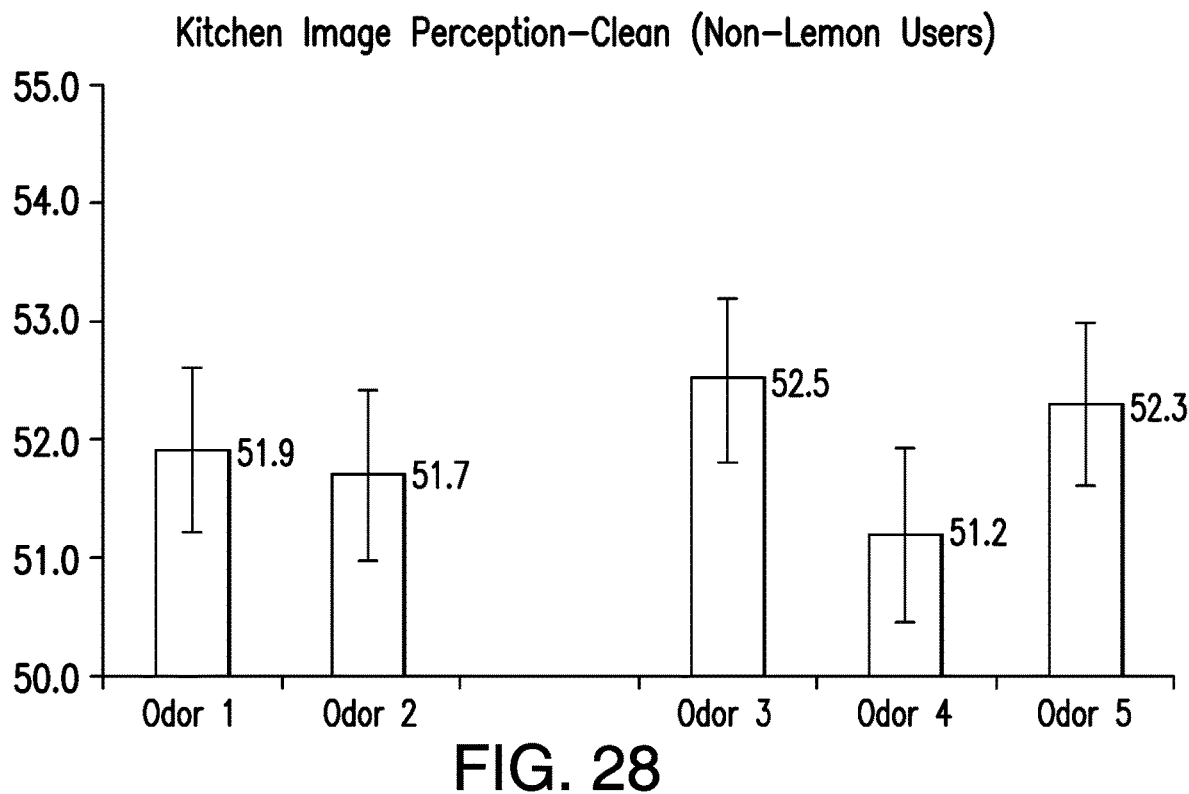
FIG. 28 shows the Non-Lemon users' perception of the hygiene attribute "clean" as described by Example 10.
Figure 29:
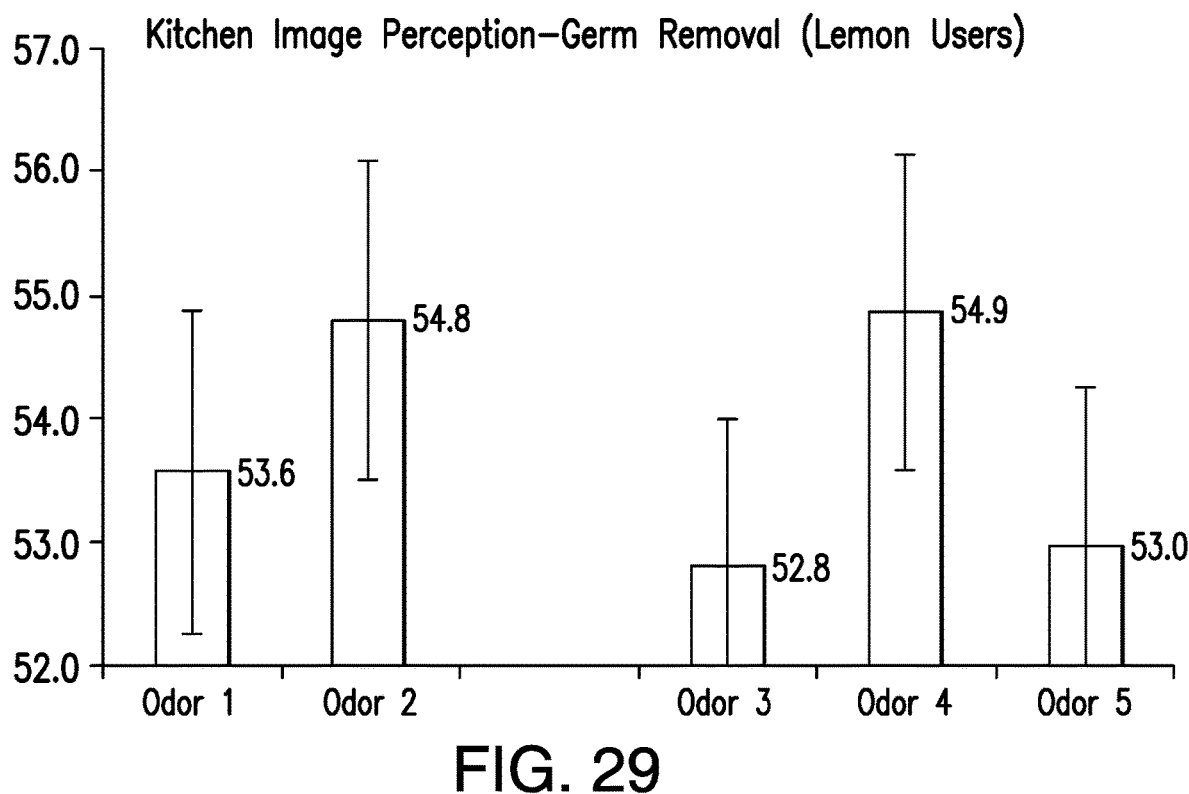
FIG. 29 shows the Lemon users' perception of the hygiene attribute "germ removal" as described by Example 10.
Figure 30:
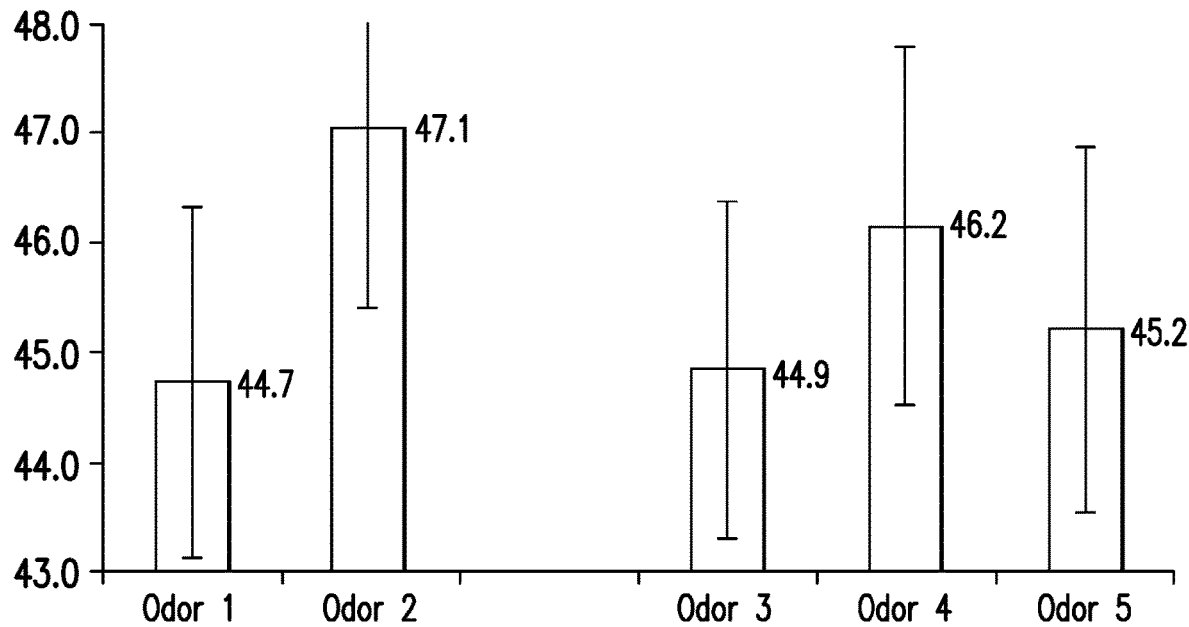
FIG. 30 shows the Lemon users' perception of the hygiene attribute "germ kill" as described by Example 10.
Figure 31:
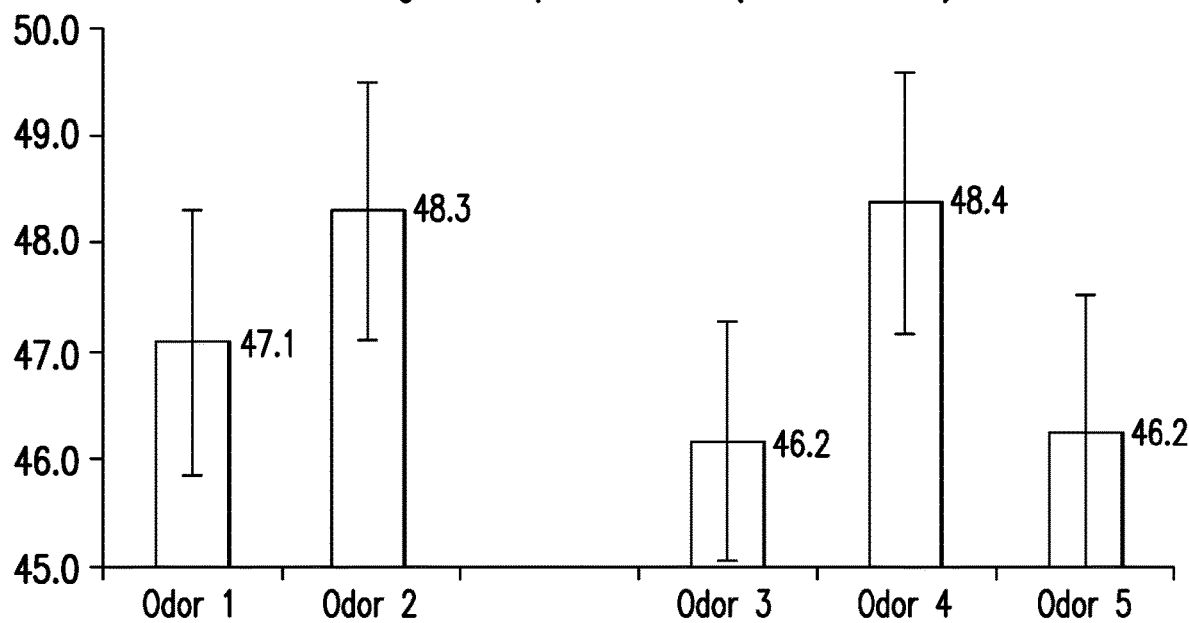
FIG. 31 shows the Lemon users' perception of the hygiene attribute "clean" as described by Example 10.

Three perceived attributes were assessed in the Cross-Modal Testing: germ removal, germ kill and clean. Because lemon oil was used as the positive control, the data was segregated by "Non-Lemon" users (i.e., "Original Clean" and "Green Tea" users combined) and "Lemon" users. As compared to the Non-Lemon users, the Lemon users were found to have a different perception profile. Results were analyzed using ANOVA F, $p<0.001$ (Odor, Image, Judge, Odor*Image, Odor*Judge, Judge*Image). Results of the Cross-Modal testing for Non-Lemon users (n=560, based on 29 participants and 18 images per odor) are shown in FIGS. 26-28. The p value of Odor in for FIG. 26 is 0.16, for FIG. 27 is 0.29, and for FIG. 28 is 0.20. Results for Lemon users (n=180, based on 10 participants and 18 images per odor) are shown in FIGS. 29-31. The p value of Odor in for FIG. 29 is 0.05, for FIG. 30 is 0.11, and for FIG. 31 is 0.17. Least Squared Means are reported in FIGS. 26-31.

The Non-Lemon users perceived Odor 3 (hygiene composition alone) and Odor 5 (Fragrance A in combination with the hygiene composition) to have improved germ removal, germ kill, and clean as compared to both controls (Odors 1 and 2) and Fragrance A alone (Odor 4). In particular, for perception of germ removal, Non-Lemon users scored Odor 3 significantly higher than Odor 4 (at 95% confidence), and directionally higher than Odor 2 (at 90% confidence). (FIG. 26). For germ removal, Odor 5 was scored directionally higher than Odor 4 (at 80% confidence). (FIG. 26). For perception of clean, Non-Lemon users scored Odor 3 significantly higher than Odor 4 (at 95% Confidence) and Odor 5 directionally higher than Odor 4 (at 80% confidence). (FIG. 28). Thus, the hygiene composition can be incorporated into an existing product to enhance the perception of hygiene.

The Lemon users generally perceived Odor 2 (the lemon oil control) and Odor 4 (Fragrance A alone) to be more hygienic. For example, for perception of germ removal, Lemon users scored both Odors 2 and 4 significantly higher than Odors 3 and 5 (at 95% confidence). (FIG. 29). For perception of germ kill, Lemon users scored Odor 2 significantly higher than Odor 1 and directionally higher than Odors 3 and 5 (at 90% confidence). (FIG. 30). For perception of clean, Lemon users scored Odors 2 and 4 directionally higher than Odors 3 and 5 (at 90% confidence). (FIG. 31).

Figure 32:
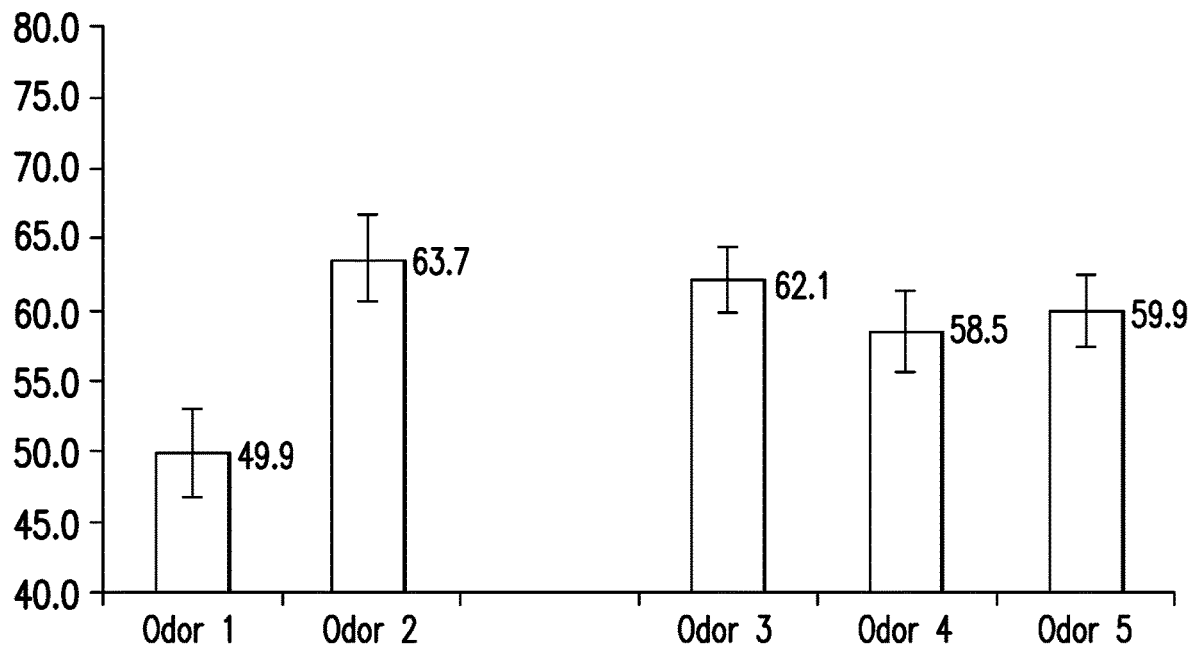
FIG. 32 shows the Non-Lemon users' average direct odor assessment scores of "cleanliness" as described by Example 10.
Figure 34:
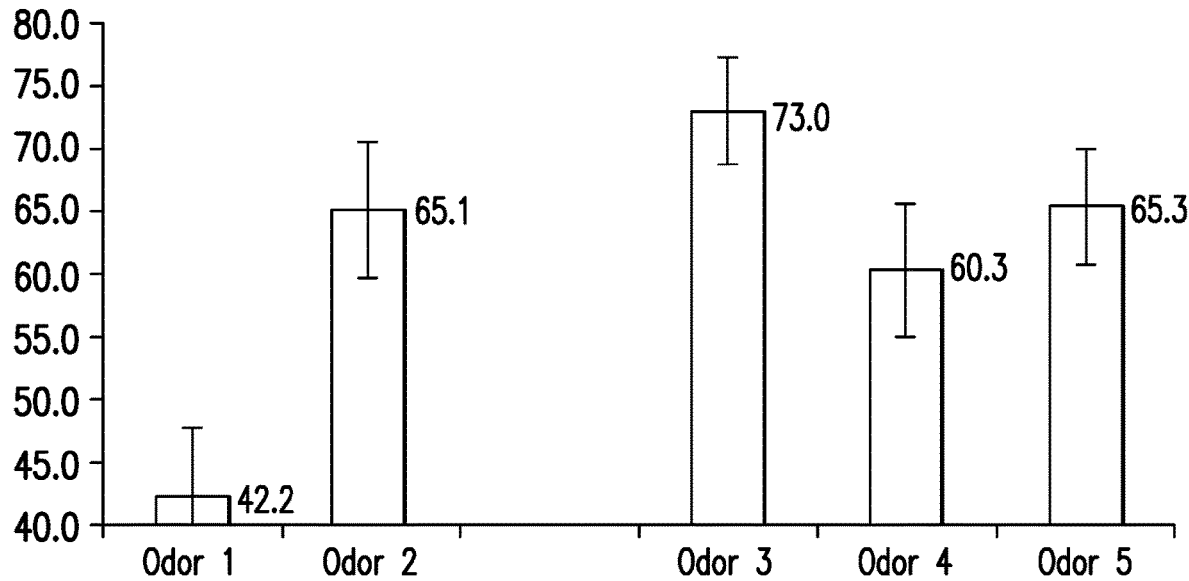
FIG. 34 shows the Lemon users' average direct odor assessment of "cleanliness" as described by Example 10.
Figure 35:
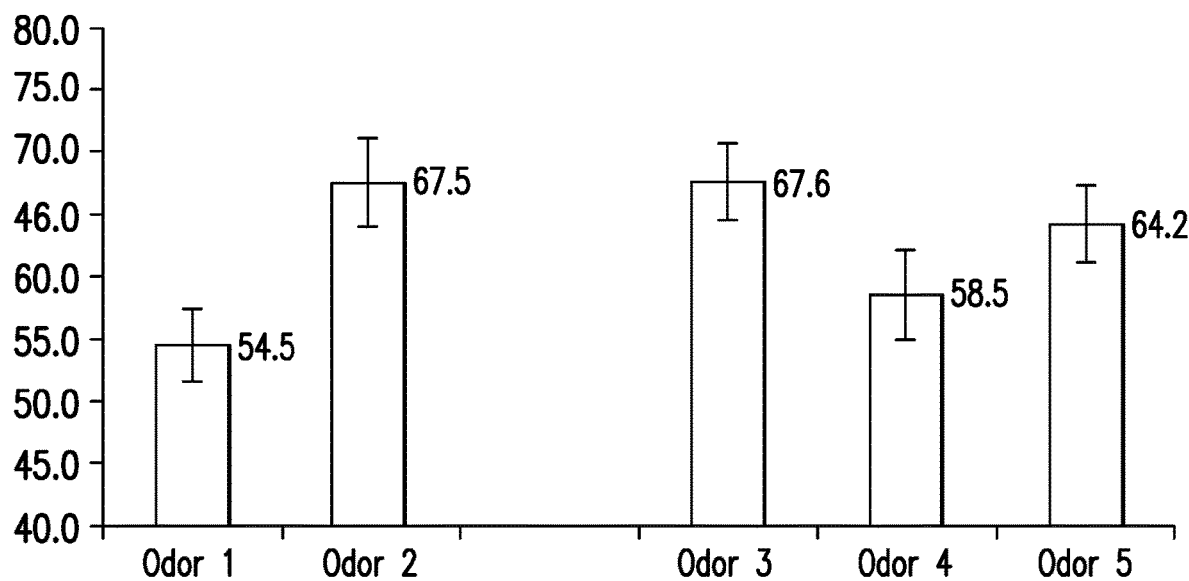
FIG. 35 shows the Lemon users' average direct odor assessment scores of "hedonicity" as described by Example 10.

Further, at the conclusion of the Cross-Modal testing, each participant was asked to score her impressions of hedonicity and cleanliness of each odor on the same scale based on a direct assessment of each odor. Results were analyzed using One Way ANOVA for Odor main effect with a p-value of <0.01. These results for Non-Lemon users (n=29) are shown in FIGS. 32 and 34 and results for Lemon users (n=10) are shown in FIGS. 34 and 35.

Figure 33:
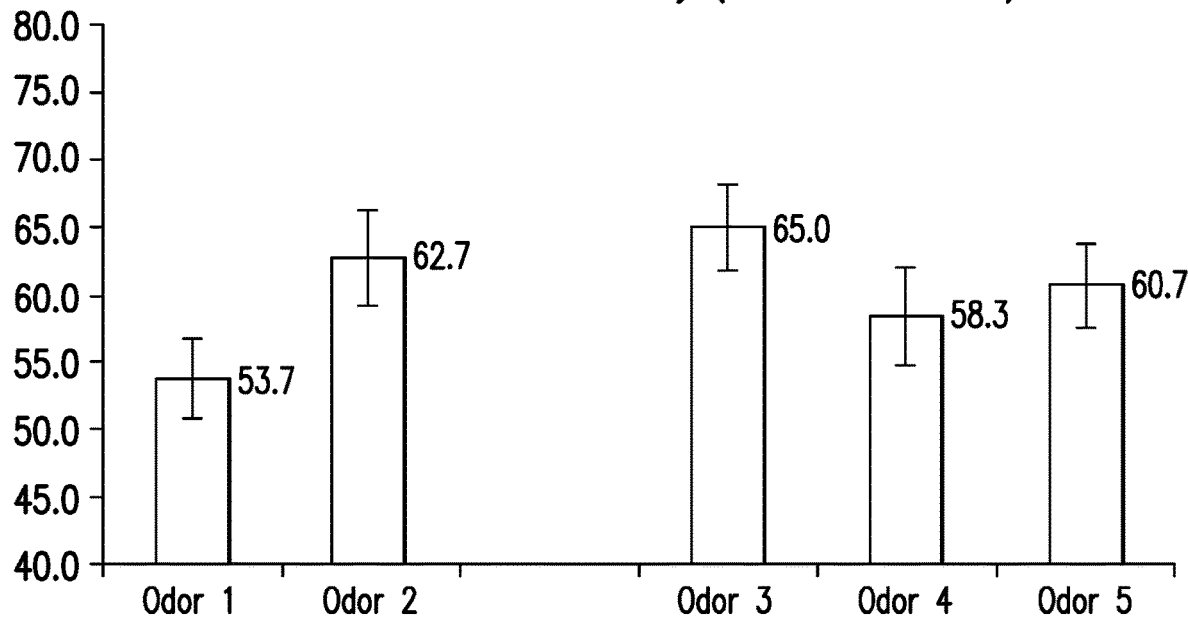
FIG. 33 shows the Non-Lemon users' average direct odor assessment scores of "hedonicity" as described by Example 10.

The Non-Lemon users reported the hygiene composition (Odor 3) to have enhanced cleanliness as compared to air (Odor 1). For example, for direct assessment of cleanliness, Non-Lemon users scored both Odors 2 and 3 significantly higher than Odor 1 (at 95% confidence). (FIG. 32). Similarly, for direct assessment of hedonicity, Odor 3 was scored significantly higher than Odor 1 (at 95% confidence). (FIG. 33). Thus, the hygiene composition was found to enhance the perception of hygiene based on direct assessments. Additionally, the Non-Lemon users reported Odor 5 to have slightly increased hedonicity as compared to Fragrance A (Odor 4). (FIG. 33). This data shows that a hygiene composition can be incorporated into a consumer product without reducing the overall likability of the product.

Although the Lemon users perceived Odor 5 to have reduced hygiene in the Cross-Modal testing, the Lemon users had generally positive direct assessments of Odor 5. For example, the Lemon users reported Odor 5 to have enhanced cleanliness as compared to Fragrance A alone (Odor 4) and air (Odor 1), and to have about the same cleanliness as lemon oil. Lemon users scored Odors 2, 3, and 5 significantly higher than Odor 1 (at 95% confidence). (FIG. 34). For perception of hedonicity, the Lemon users also scored Odors 2, 3, and 5 significantly higher than Odor 1 (at 95% confidence). Importantly, the Lemon users reported Odor 5 to have greater hedonicity than Fragrance A (Odor 4) and air (Odor 1), indicating that Lemon users generally liked Odor 5 more than Fragrance A alone. Thus, depending on a user's perceptions, a hygiene composition incorporated into a consumer product can actually improve the overall experience of the product.

Although the presently disclosed subject matter and its advantages have been described in detail, it should be understood that various changes, substitutions and alterations can be made herein without departing from the spirit and scope of the application as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the presently disclosed subject matter, processes, machines, manufacture, compositions of matter, means, methods, or steps, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, means, methods, or steps.

Patents, patent applications publications product descriptions, and protocols are cited throughout this application the disclosures of which are incorporated herein by reference in their entireties for all purposes.

What is claimed is:

1. A fragrance accord, comprising at least one of limonene thiol and cis-2-methyl-4-propyl-1,3-oxathiane, a citrus compound, an herbal/aromatic compound, a floral compound, a green compound, and a sulfur containing compound.

2. The fragrance accord of claim 1, wherein the citrus compound is present in an amount of from about 0.1% to about 80% by weight.

3. The fragrance accord of claim 1, wherein the herbal/aromatic compound is present in an amount of less than about 50% by weight.

4. The fragrance accord of claim 1, wherein the citrus compound and the herbal/aromatic compound are present in a ratio of from about 10:1 to about 0.1:1 citrus compound to herbal/aromatic compound.

5. The fragrance accord of claim 1, wherein the sulfur containing compound is selected from the group consisting of limonene thiol, thiogeraniol, 8 mercapto-p-menthan-3-one, cis-2-methyl-4-propyl-1,3-oxathiane, p-menthene-8-thiol, and combinations thereof.

6. The fragrance accord of claim 5, further comprising at least one additional sulfur containing compound selected from the group consisting of 4-methylthio-4-methyl-2-pentanone, 3 mercapto-hexanol, methoxymethylbutanethiol, dibutyl sulfide, dimethyl sufide, thiocineol, 2-isopropyl-4-methylthiazole, and combinations thereof.

7. A fragrance composition, comprising at least one fragrance accord of claim 1.

8. The fragrance composition of claim 7, wherein the fragrance accord is present in an amount of from about 0.001% to about 100% by weight of the fragrance composition.

9. The fragrance composition of claim 7, wherein the fragrance accord is present in an amount of from about 20% to about 25% by weight of the fragrance composition.

10. The fragrance composition of claim 7, comprising one or more sulfur containing compounds present in an amount from about 0.005% to about 0.1% by weight of the fragrance composition.

11. The fragrance composition of claim 10, wherein the one or more sulfur containing compounds comprise at least one of limonene thiol in an amount from about 0.000005% to about 0.00025% by weight of the fragrance composition, thiogeraniol in an amount from about 0.00002% to about 0.001% by weight of the fragrance composition, 8 mercapto-p-menthan-3-one in an amount from about 0.0005% to about 0.025% by weight of the fragrance composition, cis-2-methyl-4-propyl-1,3-oxathiane in an amount from about 0.001% to about 0.05% by weight of the fragrance composition, and p-menthene-8-thiol in an amount from about 0.0005% to about 0.025% by weight of the fragrance composition.

12. A consumer product comprising the fragrance accord of claim 1.

13. A method of stimulating a perception of hygiene in a consumer, comprising administering the fragrance accord of claim 1 to the subject in an amount effective to stimulate the perception of hygiene.

14. A method of making a consumer product capable of stimulating a perception of hygiene in a consumer, comprising:
   a. providing at least one consumer product base; and
   b. combining the consumer product base with the fragrance accord of claim 1.

15. A consumer product comprising the fragrance composition of claim 7.

16. A method of stimulating a perception of hygiene in a consumer, comprising administering the fragrance composition of claim 7 to the subject in an amount effective to stimulate the perception of hygiene.

17. A method of making a consumer product capable of stimulating a perception of hygiene in a consumer, comprising:
   a. providing at least one consumer product base; and
   b. combining the consumer product base with the fragrance composition of claim 7.

18. The fragrance accord of claim 1, wherein the floral compound is present in an amount of less than 25% by weight.

19. The fragrance accord of claim 1, wherein the green compound is present in an amount of less than 25% by weight.

\* \* \* \* \*